United States Patent [19]
Adachi et al.

[11] Patent Number: 5,880,272
[45] Date of Patent: Mar. 9, 1999

[54] OXIDIZED PHOSPHOLIPID DEGRADING ENZYME AND GENE THEREOF

[75] Inventors: Hideki Adachi, Ibaraki; Masafumi Tsujimoto, Osaka; Keizo Inoue; Hiroyuki Arai, both of Tokyo, all of Japan

[73] Assignee: Suntory Limited, Osaka, Japan

[21] Appl. No.: 961,716

[22] Filed: Oct. 31, 1997

Related U.S. Application Data

[62] Division of Ser. No. 283,917, Aug. 3, 1994.

[30] Foreign Application Priority Data

Aug. 3, 1993 [JP] Japan .................................. 5-209943

[51] Int. Cl.$^6$ .......................... C12N 15/09; C12N 15/55; C12N 9/20
[52] U.S. Cl. ......................... 536/23.2; 435/195; 435/198
[58] Field of Search .......................... 536/23.2; 435/195, 435/198

[56] References Cited

U.S. PATENT DOCUMENTS

| | | | |
|---|---|---|---|
| 5,466,595 | 11/1995 | Jones et al. | 435/240.2 |
| 5,519,003 | 5/1996 | Mochley-Rosen et al. | 514/16 |
| 5,532,152 | 7/1996 | Cousens et al. | 435/197 |
| 5,641,669 | 6/1997 | Cousens et al. | 435/195 |

FOREIGN PATENT DOCUMENTS 638646  2/1995  European Pat. Off. .

OTHER PUBLICATIONS

Stafforini DM, et al. Mammalian platelet–activating facto-racetylhydrolases. Biochim Biophys Acta. 1996 Jun. 11; 1301(3): 161–173.

Mitsuharu Hattori et al., "Purification And Characterization of Bovine Brain Platelet–Activating Factor Acetylhydrolase", The Journal of Biological Chemistry, vol. 268, No. 25, pp. 18748–18753, Sep. 5, 1993.

Mitsuharu Hattori et al., "Miller–Dieker Lissencephaly Gene Encodes A Subunit Of Brain Platelet–Activating Factor", Letters to Nature, vol. 370, pp. 216–218, Jul. 21, 1994.

Orly Reiner et al., "Isolation Of A Miller–Dieker Lissencephaly Gene Containing G Protein Beta–Subunit–Like Repeats", Letters to Nature, vol. 364, pp. 717–721, Aug. 19, 1993.

Mitsuharu Hattori et al., "The Catalytic Subunit Of Bovine Brain Platelet–Activating Factor Acetylhydrolase Is A Novel Type Of Serine Esterase", The Journal of Biological Chemistry, vol. 269, No. 37, pp. 23150–23155, Sep. 16, 1994.

Hideki Adachi et al., "cDNA Cloning Of Human Cytosolic Platelet–Activating Factor Acetylhydrolase γ–Subunit And Its mRNA Expression In Human Tissues", Biochemical and Biophysical Research Communications, vol. 214, No. 1, pp. 180–187, Sep. 5, 1995.

Mitsuharu Hattori et al., "Cloning And Expression Of A cDNA Encoding The Beta–Subunit (30–kDa Subunit) Of Bovine Brain Platelet–Activating Factor Acetylhydrolase", The Journal of Biological Chemistry, vol. 270, No. 52, pp. 31345–31352, Sep. 29, 1995.

Sevanian et al., "Metabolism Of Epoxidized Phosphatidylcholine By Phospholipase $A_2$ And Epoxide Hydrolase", Lipids, vol. 16, No. 11, pp. 781–789, (1981).

Miwa et al., "Characterization Of Serum Platelet–Activating Factor (PAF) Acetylhydrolase", J. Clin. Invets., vol. 82, pp. 1983–1991, (1988).

Yanoshita et al., "Hydrolysis Of Platelet Activating Factor And Its Methylated Analogs By Acetylhydrolases", J. Biochem., vol. 103, No. 5, pp. 815–819, (1988).

Stafforini et al., The Platelet–Activating Factor Acetylhydrolase From Human Erythrocytes, J. Biol. Chem., vol. 268, No. 6, pp. 3857–3865, (1993).

Banerjee et al., "inhA, A Gene Encoding A Target For Isoniazid And Ethionamide In *Mycobacterium Tuberculosis*", Science, vol. 263, pp. 227–230, (1994).

Tjoelker et al., "Anti–Inflammatory Properties Of A Platelet–Activating Factor Acetylhydrolase", Nature, vol. 374, pp. 549–553, (1995).

Bazan, A Signal Terminator, Nature, vol. 374, pp. 501–502, (1995).

Primary Examiner—Keith D. Hendricks
Assistant Examiner—Bradley S. Mayhew
Attorney, Agent, or Firm—Oblon, Spivak, McClelland, Maier & Neustadt, P.C.

[57] ABSTRACT

An oxidized phospholipid degrading enzyme is provided, which plays an important role in the oxygen stress preventive mechanism in organisms. The enzyme hydrolyzes a 1-acyl-2-ω-carboxyfatty acid acyl-3-phosphatidylcholine as a substrate at the 2-ester bond thereof to form 1-acyl-2-lyso-3-phosphatidylcholine. The activity of the enzyme is slightly enhanced by 4 mM calcium chloride. The molecular mass of the enzyme is 95±5 kDa (by gel filtration). The enzyme is composed of three subunits whose molecular masses have been found to be 29 kDa, 30 kDa and 45 kDa, respectively, by SDS-polyacrylamide electrophoresis. A gene coding the enzyme is also provided. This gene is important for the synthesis of the enzyme by genetic engineering.

6 Claims, 6 Drawing Sheets

OXIDIZED PHOSPHOLIPID DEGRADING ENZYME AND GENE THEREOF

This is a Division of application Ser. No. 08/283,917 filed on Aug. 3, 1994, now pending.

BACKGROUND OF THE INVENTION a) Field of the Invention

This invention relates to a novel phospholipase, and more specifically to an oxidized phospholipid degrading enzyme playing an important role in the oxidized phospholipid elimination mechanism in animal cytoplasm and also to a gene coding the same.

b) Description of the Related Art

It is known that under diverse oxygen stress, a phospholipid as a membrane-forming component is oxidized to cause various troubles on an organism. The organism is considered to be equipped with a protective mechanism against such oxygen stress so that an oxidized phospholipid formed under oxygen stress would be promptly hydrolyzed by an oxidized phospholipid degrading enzyme to avoid any trouble, which could otherwise occur by a chain oxidative reaction, and also to facilitate restoration of phospholipid molecules.

Regarding the oxidized phospholipid degrading enzyme playing the important role in the protective mechanism, there is the view that phospholipase $A_2$ known to catalyze the splitting of normal phospholipids also plays the role (Sevanian, A., Stein, R. A. and Mead, J. F., Lipids 16, 781–789, 1981). For the low oxidized-phospholipid degrading activity of phospholipase $A_2$, however, it has been considered that another enzyme plays this role in actual organisms.

BRIEF DESCRIPTION OF THE INVENTION

To prevent various troubles caused by oxygen stress in an organism, it is necessary as a first step to elucidate the protective mechanism against oxygen stress in the organism and to identify an oxidized phospholipid degrading enzyme which takes part in the protective mechanism.

The present inventors started research with a view toward isolating and purifying an oxidized phospholipid degrading enzyme which exists in a tissue of an organism. First, it was however found that TLC (thin-layer chromatography), which is a conventional method for the assay of oxidized phospholipid degrading enzymes, would be able to measure only 12 samples or so at once and moreover, would take as long as 5 hours until the results are obtained and hence is not usable in view of the number of samples, deactivation of purified enzymes, etc.

An investigation was therefore conducted to devise a new method for the assay of oxidized phospholipid degrading enzymes and as a method permitting assay of 40 samples or so at once in a period as short as 2 hours or so, a method making use of $^{14}C$-labeled oxidized phosphatidylcholine (oxidized PC) as a substrate was developed.

As a result of a further investigation, it was found that an oxidized phospholipid degrading enzyme also uses 1-hexadecyl-2-acetyl-sn-glycero-3-phosphocholine (platelet activating factor, PAF) as a substrate like oxidized PC. Based on this finding, the present inventors also developed a method for the assay of an oxidized phospholipid degrading enzyme, said method making use of $^3H$-labeled PAF as a substrate.

The above method which makes use of PAF has advantages over the above-described system making use of oxidized PC, such as (1) since PAF is a simple substance, the system can be simplified compared with the use of oxidized PC which is a mixture, (2) because the product of hydrolysis at sn-2 is acetic acid, this hydrolyzate can be separated completely from unreacted PAF by devising solvent fractionation as needed, and (3) for the availability of $^3H$-labeled PAF on the market, a stable assay system can be constructed.

By the above assay method, the present inventors measured the oxidized phospholipid degrading enzyme activity in soluble fractions of various organs of animals, leading to the finding that the enzyme activity is distributed widely in organs such as brain and kidneys.

The present inventors then chose bovine brain as a source for the provision of an oxidized phospholipid degrading enzyme and by using a variety of isolation and purification methods, increased its purity while monitoring its enzyme activity by the assay method described above. As a result, an oxidized phospholipid degrading enzyme has been obtained in a substantially pure form.

Further, a gene which codes the oxidized phospholipid degrading enzyme has also been found by a known method from the peptide sequence of the enzyme.

The present invention has been completed based on these findings, and provides the oxidized phospholipid degrading enzyme—which plays an important role in the oxygen stress preventive mechanism in organisms—and also the gene coding the enzyme, said gene being important for the synthesis of the enzyme by genetic engineering.

The oxidized phospholipid degrading enzyme according to this invention selectively degrade an oxidized phospholipid, whereby it can be used as a pharmaceutical or biochemical reagent for the prevention or treatment of diseases caused by oxidation of a phospholipid in an organism, for example, tissue damages due to ischemic re-perfusion, inflammation, hepatophathy by an organic chlorine compound or the like, and adult respiratory distress syndrome.

The gene which codes the oxidized phospholipid degrading enzyme according to this invention makes it possible to obtain the enzyme of this invention in a large quantity by conducting its expression in a host such as *E. coli* by gene manipulation.

It is also possible to construct an assay system for the evaluation of each oxidized phospholipid elimination mechanism by introducing the above gene in CHO cells or the like.

DETAILED DESCRIPTION OF THE INVENTION

Figure 1:
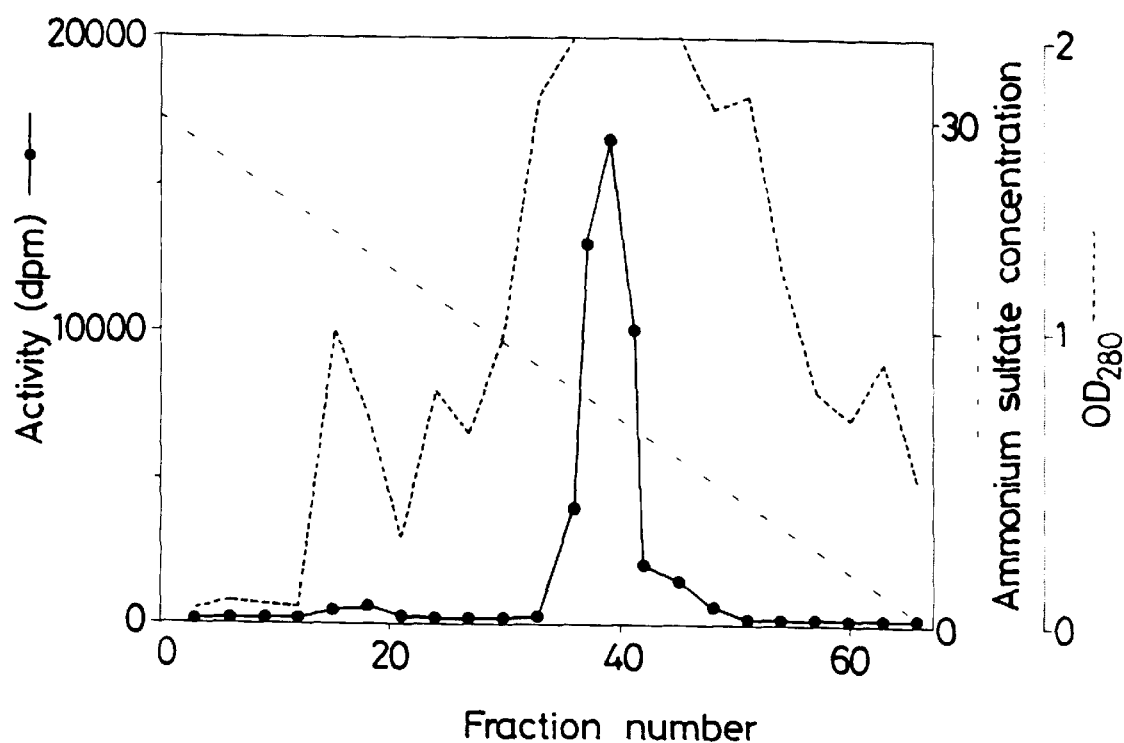
FIG. 1 is a diagram showing chromatography on a "BUTYL TOYOPEARL" column.

Although the oxidized phospholipid degrading enzyme according to the present invention can be obtained from various tissues of animals or the like containing the enzyme by isolating and purifying it in a manner known per se in the art while using the oxidized phospholipid degrading activity as an index, it is preferred to use bovine brain for the reasons to be described next.

In the brain, (1) the concentration of α-tocopherol (vitamin E), an important antioxidant, is low compared with other organs (Faud, J. and McNally, W. P., Arch. Int. Parmacodyn. 250, 4–17, 1981), (2) ischemic re-perfusion often occurs, (3) the oxygen consumption per unit weight is far higher compared with other organs, and (4) for reasons such that cranial nerve cells undergo a severe damage once a trouble occurs because they are practically unregenerated through divisions, the content of an oxidized phospholipid degrading enzyme effective for the prevention of this trouble is expected to be high.

Further, to obtain an enzyme whose content is low in an organism, a great deal of raw material is needed. As a large animal which now enables easy provision of a large number of brains, bovine is most suited.

It is therefore preferred to use bovine brains as a raw material for the provision of the oxidized phospholipid degrading enzyme.

Using bovine brains as an illustrative raw material, a specific description will hereinafter be made of procedures for obtaining the oxidized phospholipid degrading enzyme.

As bovine brains to be used as a raw material for the provision of the oxidized phospholipid degrading enzyme, is used gray matter which remains after removal of surface blood vessels, white matter and diencephalon from whole bovine brains immediately after slaughter.

After these bovine brains are washed with a suitable buffer (for example, 10 mM Tris-HCl buffer containing 250 mM sucrose and 1 mM EDTA and having a pH of 7.4), they were homogenized with the same buffer and then centrifuged to obtain a soluble fraction of cytoplasm.

The soluble fraction of cytoplasm is fractionated with ammonium sulfate by a method known per se in the art, thereby obtaining a 45%–60% pellet (i.e., a precipitate fraction formed when ammonium sulfate is added to a 45% saturation supernatant until the concentration of ammonium sulfate reaches 60% saturation).

While making combined use of hydrophobic chromatography, ion exchange chromatography, adsorption chromatography, gel filtration chromatography and the like, this pellet fraction is purified until a single peak is obtained on a "Superose 12 Column" (Pharmacia AB), so that the oxidized phospholipid degrading enzyme can be obtained.

The enzyme so obtained had the following physical and chemical properties:

(1) Action:

The enzyme hydrolyzes a 1-acyl-2-ω-carboxyfatty acid acyl-3-phosphatidylcholine as a substrate at the 2-ester bond thereof to form 1-acyl-2-lyso-3-phosphatidylcholine.

(2) Substrate specificity:

The enzyme hydrolyzes a 1,2-diacyl-3-phosphatidylcholine in which the 2-acyl group is a ω-carboxyfatty acid acyl group or an acetyl group, but does not hydrolyze a 1,2-diacyl-3-phosphatidylcholine in which the 2-acyl group is a fatty acid acyl group having at least 6 carbon atoms.

(3) Optimal reaction pH:

pH 7.0 to 8.0

(4) Inhibitors:

Enzyme reactions are inhibited by 1 mM p-bromophenacyl bromide (BPB) or 1 mM diisopropylfluorophosphate (DFP) but are not inhibited by 1 mM iodoacetamide (IAM).

(5) Activation by calcium ions:

Enzyme activity is slightly enhanced by 4 mM calcium chloride.

(6) Molecular mass:

95±5 kDa (by gel filtration).

(7) Subunits:

The enzyme is composed of three subunits whose molecular masses have been found to be 29 kDa, 30 kDa and 45 kDa, respectively, by SDS-polyacrylamide electrophoresis.

As described above under (7) and will also be described in detail in Examples, the oxidized phospholipid degrading enzyme has been ascertained from the results of SDS-polyacrylamide electrophoresis (SDS-PAGE) to be a heterotrimer composed of three subunits of 45 kDa, 30 kDa and 29 kDa, respectively.

By subjecting the above enzyme to treatment on a heparin Sepharose column or sulfated Cellulofine column, a 30 kDa–29 kDa complex without the 45 kDa subunit was obtained. The complex so obtained exhibited similar activity.

On the other hand, reaction of the enzyme with $^3$H-labeled diisopropylfluorophosphate results in specific labeling of the 29 kDa subunit, so that the activity of the enzyme is considered to be attributed to active serine residual groups contained in the subunit. Accordingly, the 29 kDa subunit can be used by itself as a synthesized oxidized phospholipid degrading enzyme or the like.

To determine the primary structure of each of he subunits making up the oxidized phospholipid degrading enzyme of this invention, it is only necessary to subject their corresponding full-length cDNA's to cloning to determine the base sequences of the cDNA's and then to determine amino acid sequences corresponding to the base sequences, respectively.

Described specifically, the enzyme according to this invention is degraded to obtain peptide fragments corresponding to the respective subunits and their amino acid sequences are determined. Oligomers having base sequences corresponding to the respective amino acid sequences are then synthesized. Using PCR, full-length cDNA's are cloned from a cDNA library.

The base sequences of the full-length cDNA's are determined by an automated sequencer. Subsequent to estimation of coding initiator codons, the corresponding amino acid sequences are determined so that the amino acid sequences of the respective subunits can be determined.

The thus-obtained base sequences of the genes which code the individual subunits of the above enzyme are as shown in a Sequence Listing to be described subsequently herein, namely, the 29 kDa subunit is represented by Sequence 4, the 30 kDa subunit by Sequence 6, and the 45 kDa subunit by Sequence 7, respectively.

Further, the amino acid sequences of the respective subunits of the above enzyme, said amino acid sequences being estimated from the above base sequences, are also as shown in the Sequence Listing, namely, the 29 kDa subunit is represented by Sequence 1, the 30 kDa subunit by Sequence 2, and the 45 kDa subunit by Sequence 3, respectively.

The term "an amino acid sequence having homology" as used herein means that the amino acid sequence has the same function as the peptide represented by the preceding amino acid sequence although the former sequence have at parts thereof substitution, deletion, addition and/or the like of amino acids.

The oxidized phospholipid degrading enzyme of this invention obtained as described above selectively degrades oxidized phospholipids as demonstrated in the Examples to be described subsequently herein.

The enzyme is therefore believed to degrade an oxidized phospholipid formed as a result of oxidation of plasma membranes or organelle membranes so that it protects membranes from damages, which would otherwise occur by a chain oxidative reaction, and also to promote restoration of phospholipid molecules.

The present invention will hereinafter be described in further detail by the following Examples and Reference Examples. It should however be borne in mind that the present invention is by no means limited to or by such Examples.

REFERENCE EXAMPLE 1

Preparation of Substrate for the Oxidized Phospholipid Degrading Enzyme:

(a) Synthesis of 1-palmitoyl-2-[1-$^{14}$C]-linoleoyl-sn-glycero-3-phosphocholine (2-$^{14}$C-linoleoyl PC)

Mixed were 5 µmol of 1-palmitoyl-sn-glycero-3-phosphocholine (lyso PC) (product of Bachem Feinchemikalien AG) and 3.5 µmol (203 µCi) of [1-$^{14}$C]-linoleic acid (product of New England Nuclear Company]. Subsequent to evaporation, the resulting mixture was suspended in 6.25 ml of a phosphated buffer (pH 7.4).

The suspension was then added with 1.5 ml of a microsome fraction (7.2 mg/ml) of rat liver, 1.25 ml of 100 mM ATP, 1.25 ml of 100 mM $MgCl_2$ and 0.75 ml of 5 mM CoA, followed by incubation at 37° C. for 30 minutes. After total lipids were extracted by the Bligh-Dyer method (Bligh, E. G. and Dyer, W. J., Can. J. Biochem. Physiol., 37, 911, 1959), the solvent was distilled off.

The residue was dissolved in a small amount of chloroform and then applied to chromatography on a "CM Cellulose 52 Column" (1.5×5.0 cm) (product of Whatman Company). The column was washed with a chloroform-methanol (99:1) solvent system to elute unreacted linoleic acid, followed by the elution with a chloroform-methanol (96:4) solvent system. While monitoring by TLC, the whole eluate fractions were collected. Subsequent to elimination of the solvent, the residue was dissolved in a chloroform-methanol (2:1) solvent system and was then stored. The recovery rate of radioactivity was about 55%.

(b) Adjustment of Specific Radioactivity and Oxidation

The 2-$^{14}$C linoleoyl PC (hot) obtained above in step (a) and non-radioactive (cold) 2-linoleoyl PC (product of Serdary Research Laboratories Inc.) were mixed to adjust the specific radioactivity to about 3,000 dpm/nmol. Following the method proposed by Gerlach et al. (Gerlach, E. and Deuticke, B., Biochem. J., 337, 447, 1969), phosphorus was quantitatively analyzed to determine the exact specific radioactivity.

Subsequent to the adjustment of the specific radioactivity, the PC was oxidized following the procedures proposed by Shimojo et al. (Shimojo, T., Abe, M. and Ohta, M., J. Lipid Res., 15, 525–527, 1974), Described specifically, the solvent was removed from 7.5 µmol of the PC which had been adjusted in specific radioactivity, followed by the dissolution of the residue in 1.5 ml of 90% acetic acid. To the solution, an oxidizing solution which was an aqueous solution of 24 mM potassium permanganate and 20 mM of sodium periodate was added 200 µl by 200 µl 20 times (4 ml in total) under stirring. The resulting mixture was stirred at room temperature for 2 hours.

After completion of the reaction, a small amount of 20% sodium sulfite was added to deactivate any unreacted oxidizing agents. The resulting mixture was adjusted to pH 2 with 1N hydrochloric acid and then extracted three times by the Bligh-Dyer method. All the extracts were combined, from which the solvent was eliminated. The residue was dissolved in a small amount of chloroform and then applied to a thin-layer chromatography (TLC) while using preparative silica gel plates. The residue was developed by a chloroform-methanol-ammonia (65:35:10) mixture. As controls, standard samples of 2-linoleoyl PC and 2-azelaoyl PC were also developed.

After the development, plates corresponding to oxidized PC were collected with reference the positions of the controls identified by iodine staining and the distribution of radioactivity determined by a TLC scanner. Under acidic conditions of acetic acid, those plates were subjected three times to extraction by the Bligh-Dyer method. After the solvent was eliminated, the residue was dissolved in a chloroform-methanol (2:1) solvent system and then stored at −20° C.

REFERENCE EXAMPLE 2

Measurement of the Activity of the Oxidized Phospholipid Degrading Enzyme by Using Oxidized PC To measure the activity of the oxidized phospholipid degrading enzyme by using oxidized PC, Tris-HCl buffer (final concentration: 50 mM, pH 7.4) which contained as a substrate 20 nmol (6,000 dpm) of the oxidized PC obtained in Reference Example 1 was added with 5 mM EDTA or 4 mM $CaCl_2$ as needed, to which the sample (enzyme source) to be measured was added to give a total volume of 250 µl.

They were mixed in a test tube over ice and then incubated at 37° C. for 30 minutes. Thereafter, 560 µl of a chloroform-methanol (1:1) mixture were added to terminate the reaction. After the resulting mixture was vigorously mixed for 5 minutes by a vortex stirrer, the mixture was centrifuged for 5 minutes at 3,000 rpm to separate it into two layers. From the upper layer, 300 µl were collected, in which 3 ml of "Clearsol I" (product of NACALAI TESQUE INC.) were mixed. The radioactivity was measured by a liquid scintillation counter. From the intensity of the radioactivity, the amount of the dicarboxylic acid formed as a result of 2-hydrolysis was calculated to determine the enzyme activity.

REFERENCE EXAMPLE 3

Measurement of the Activity of the Oxidized Phospholipid Degrading Enzyme by Using PAF (a) Preparation of substrate 1-Hexadecyl-2-[$^3$H]acetyl-sn-glycero-3-phosphocholine (hot PAF, product of Bachem Feinchemikalien AG) and non-radioactive PAF (cold PAF) were mixed to adjust the specific radioactivity to about 3,000 dpm/nmol. Phosphorus was quantitatively analyzed likewise to measure the exact specific radioactivity.

(b) Measurement of the activity of the oxidized phospholipid degrading enzyme by using PAF Measurement of the oxidized phospholipid degrading enzyme by using PAF was conducted in a similar manner to Reference Example 2. Namely, Tris-HCl buffer (final concentration: 50 mM, pH 7.4) which contained as a substrate 20 nmol (6,000 dpm) of the labeled PAF obtained in step (a) was added with 5 mM EDTA or 4 mM $CaCl_2$ as needed, to which the sample (enzyme source) to be measured was added to give a total volume of 250 μl.

They were mixed in a test tube over ice and then incubated at 37° C. for 30 minutes. Thereafter, 2.5 ml of a chloroform-methanol (4:1) mixture were added to terminate the reaction. Subsequent to addition of 0.25 ml of water, the resulting mixture was vigorously mixed for 5 minutes by a vortex stirrer and then centrifuged for 5 minutes at 3,000 rpm to separate it into two layers. From the upper layer, 600 μl were collected, in which 3 ml of "Clearsol I" (product of NACALAI TESQUE INC.) were mixed. The radioactivity was measured by a liquid scintillation counter. From the intensity of the radioactivity, the amount of acetic acid formed as a result of 2-hydrolysis was calculated to determine the enzyme activity.

EXAMPLE 1

Purification of the Oxidized Phospholipid Degrading Enzyme from Bovine Brain (a) Preparation of soluble fraction of cytoplasm of bovine brain Surface blood vessels, white matter and diencephalon were removed from about 500 g of bovine brain, whereby about 300 g of gray matter were obtained. After it was washed three times with 10 mM Tris-HCl buffer containing 250 mM sucrose and 1 mM EDTA (pH 7.4, hereinafter called the "SET buffer"), about 600 ml of the SET buffer were added, followed by homogenization for 30 seconds in a "National Mixer, Model:MX-V350".

The above procedures were repeated 5 times in total. The resulting homogenate was centrifuged for 20 minutes in a TOMMY centrifugal machine (No. 9, 10 krpm) to remove solid matter. The supernatant so formed was subjected to 100,000 g's ultracentrifugation ("Hitachi-70P, RP42" rotor, 40 krpm) so that about 570 ml of a soluble fraction of cytoplasm of bovine brain was obtained. The protein concentration measured by the Lowry method was about 11.6 mg/ml.

(b) Fractionation with ammonium sulfate

To 300 ml of the soluble fraction of the cytoplasm of the bovine brain obtained above in step (a), solid ammonium sulfate (enzyme purification grade, product of WAKO PURE CHEMICAL INDUSTRIES, LTD.) was added little by little in ice water under stirring by a method known per se in the art so that the concentration of ammonium sulfate reached 45% saturation in terms of the Osborne's saturation degree. After the completion of the addition, the resulting mixture was stirred for further 30 minutes. The mixture so obtained was then centrifuged for 20 minutes in the TOMMY centrifugal machine (No. 9, 10 krpm) to separate it into a precipitate and a supernatant. Solid ammonium sulfate was added further to the supernatant to give 60% saturation. The resulting mixture was treated similarly to obtain a precipitate (this fraction will be called "45–60% pellet").

(c) "Butyl TOYOPEARL" column chromatography

The 45–60% pellet obtained above in step (b) was suspended in 150 ml of 10 mM Tris-HCl buffer which contained 1 mM EDTA. The suspension was then dialyzed against 5,000 ml of the same buffer. After the dialysis, ammonium sulfate was added to 30% saturation and a precipitate formed in a small amount was removed by centrifugation (3,500 rpm, 10 minutes). The supernatant of the centrifugation was applied to a 2.5× 18 cm column packed with "Butyl TOYO-PEARL 650 M" (product of TOSOH CORPORATION) which had been equilibrated with the above buffer containing ammonium sulfate at 30% saturation. The column was washed with the above buffer containing 30% saturation of ammonium sulfate, followed by elution with a 500 ml linear gradient of ammonium sulfate (from 30% saturation to 0% saturation) in the above buffer.

While monitoring by 280 nm ultraviolet absorption, the eluate was fractionated 8 ml by 8 ml. The activity of each fraction was measured with a PAF system which contained 5 mM EDTA. A main active fraction was observed in registration with an ultraviolet absorption peak of a fraction eluted around 10% saturation ammonium sulfate concentration.

The results are shown in FIG. 1.

(d) "DEAE Sepharose CL-6B" column chromatography

The active fraction obtained above in step (c) was dialyzed against 5,000 ml of 10 mM Tris-HCl buffer (pH 7.4, hereafter called TEG buffer) which contained 1 mM EDTA and 10% glycerol. After the dialysis, the dialyzed solution was applied to a column (1.5×15 cm) packed with "DEAE Sepharose CL-6B" (product of Pharmacia AB) which had been equilibrated with TEG buffer. The column was washed with TEG buffer, followed by elution with a 400 ml linear gradient of NaCl (0 mM to 300 mM) in TEG buffer.

While monitoring by 280 nm ultraviolet absorption, the eluate was fractionated 6 ml by 6 ml. The activity of each fraction was measured with a PAF system which contained 5 mM EDTA. A main active fraction was observed around 130 mM NaCl concentration separately from an ultraviolet absorption peak.

Figure 2:
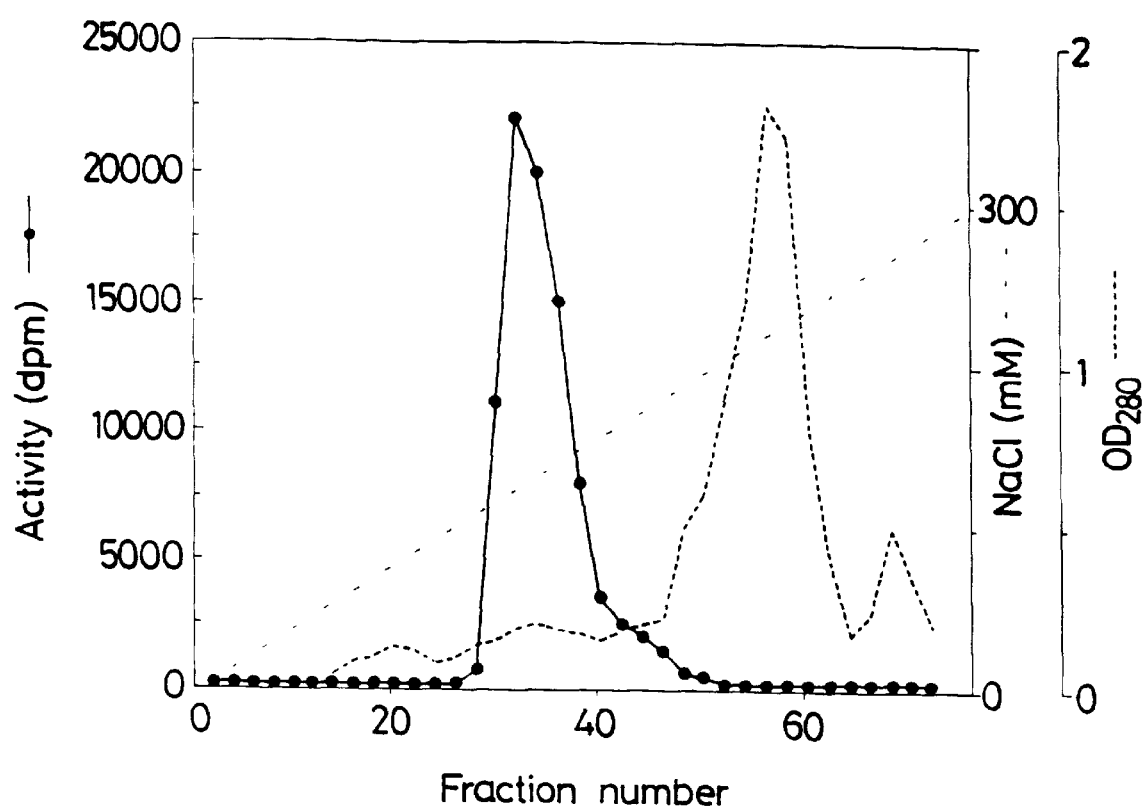
FIG. 2 is a diagram showing chromatography on a "DEAE Sepharose CL-6B" column.

The results are shown in FIG. 2.

(e) Hydroxyapatite column chromatography

The active fraction obtained above in step (d) was applied, as was, to a hydroxyapatite column (1.5×15 cm) which had been equilibrated with potassium-phosphated buffer (pH 6.8, hereinafter called "buffer A") which contained 5 mM 2-mercaptoethanol and 10% glycerin. The column was washed with buffer A, followed by elution with a 400 ml linear gradient of $KH_2PO_4$—KOH (10 mM to 300 mM).

While monitoring by 280 nm ultraviolet absorption, the eluate was fractionated 6 ml by 6 ml. The activity of each fraction was measured with a PAF system which contained 5 mM EDTA. A main active fraction was observed around a $KH_2PO_4$—KOH concentration of 110 mM in registration with an ultraviolet absorption peak. The purity of the enzyme in this purification step was about 70%.

Figure 3:
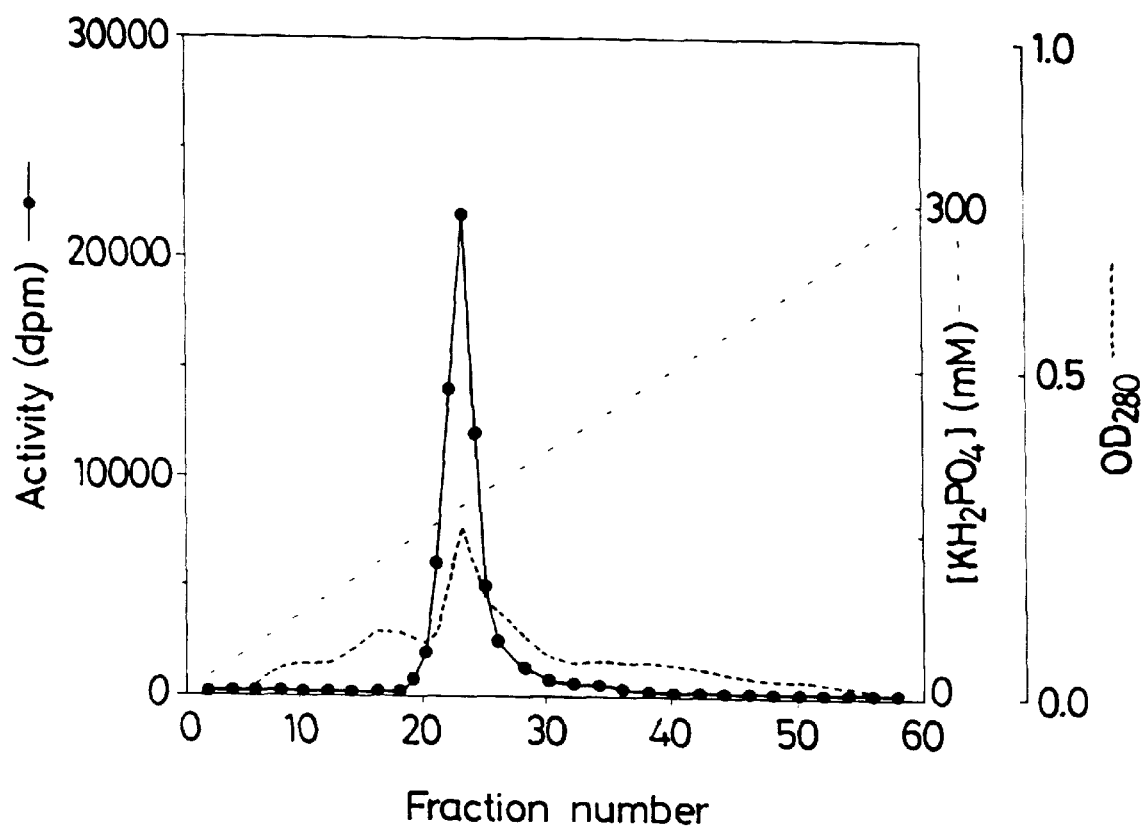
FIG. 3 is a diagram showing chromatography on a "hydroxyapatite" column.

The results are shown in FIG. 3.

(f) "Mono Q FPLC" column chromatography

The active fraction obtained above in step (e) was dialyzed against 3,000 ml of buffer A. Using an "FPLC system" (product of Pharmacia AB), the dialyzed solution was caused to adsorb at a flow rate of 0.5 ml/min on a "mono Q column" which had been equilibrated with buffer A. The column was washed at the same flow rate with 10 ml of buffer A, followed by elution with a 28 ml linear gradient of NaCl (0 mM to 200 mM) in buffer A.

While monitoring by 280 nm ultraviolet absorption, the eluate was fractionated 0.5 ml by 0.5 ml. The activity of each fraction was measured with a PAF system which contained 5 mM EDTA. A main active fraction was observed around an NaCl concentration of 125 mM in registration with an ultraviolet absorption peak.

Figure 4:
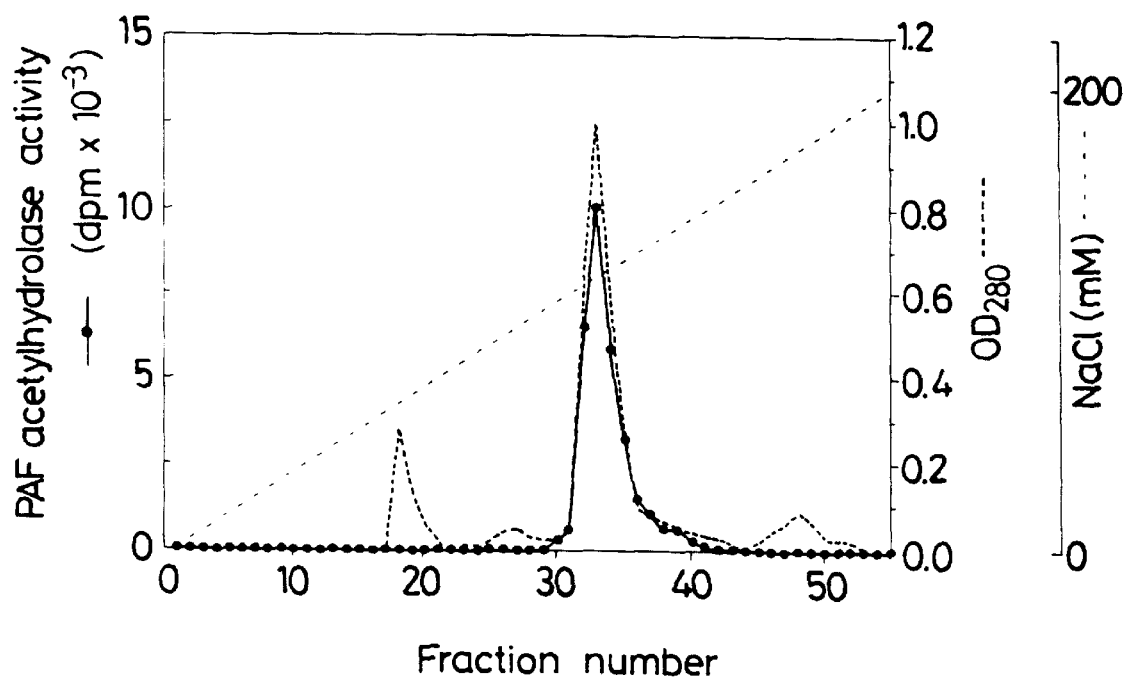
FIG. 4 is a diagram showing chromatography on a "mono Q FPLC" column.

The results are shown in FIG. 4.

(g) Verification of the purity by gel filtration of the purified sample

Figure 5:
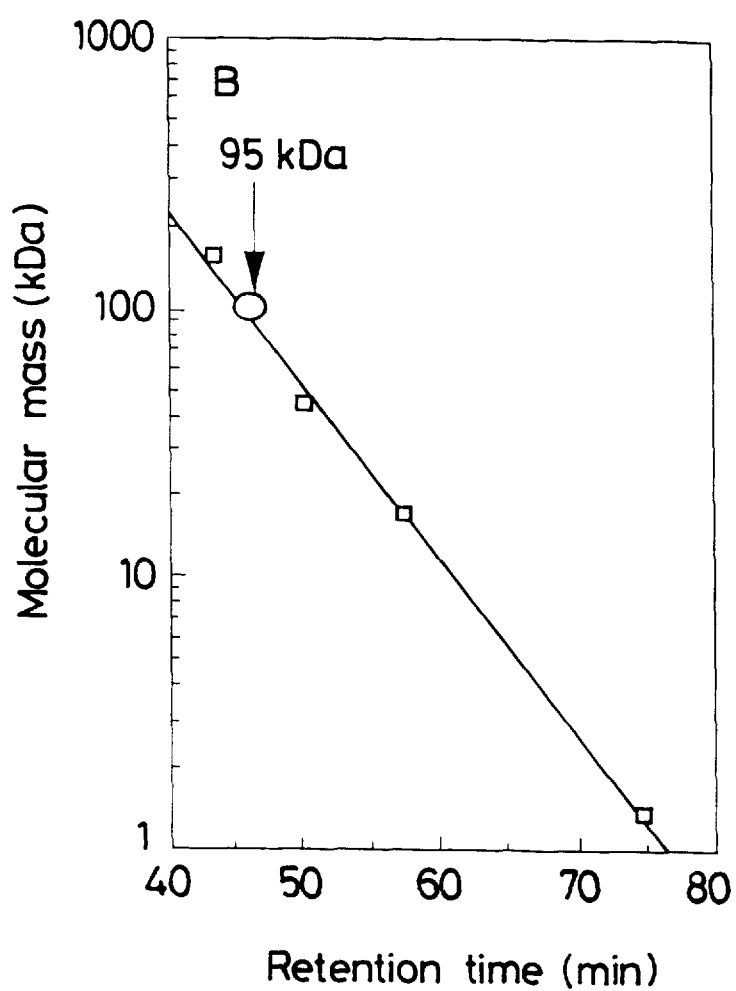
FIG. 5 is a diagram showing the results of gel filtration.

Using the FPLC system, 100 μl of the active fraction obtained above in step (f) were applied at a flow rate of 0.25 ml/min on a "Superose 12 Column" (product of Pharmacia AB) which had been equilibrated with buffer A. When the column was developed at the same flow rate while monitoring by 280 nm ultraviolet absorption, a single-peak absorption was observed at 95 kDa as illustrated in FIG. 5. Enzyme activity was also observed in registration with that peak.

Purification data obtained in various purification steps described so far are presented in Table 1.

TABLE 1

| Purification step | Total* activity | Total proteins (mg) | Specific** activity | Purification degree (times) | Recovery rate (%) |
|---|---|---|---|---|---|
| Soluble fraction | 4800 | 6600 | 0.72 | 1 | 100 |
| Ammonium sulfate fractionation | 3360 | 690 | 4.9 | 6.8 | 70.0 |
| Butyl TOYOPEARL | 1520 | 81 | 18.8 | 26.3 | 31.7 |
| DEAE Sepharose | 1210 | 2.7 | 448 | 622 | 25.2 |
| Hydroxy-apatite | 907 | 0.9 | 1008 | 1400 | 18.9 |
| Mono Q FPLC | 435 | 0.3 | 1450 | 2010 | 9.1 |

*unit: nmol/min.
**unit: nmol/min/mg.

EXAMPLE 2

Figure 6:
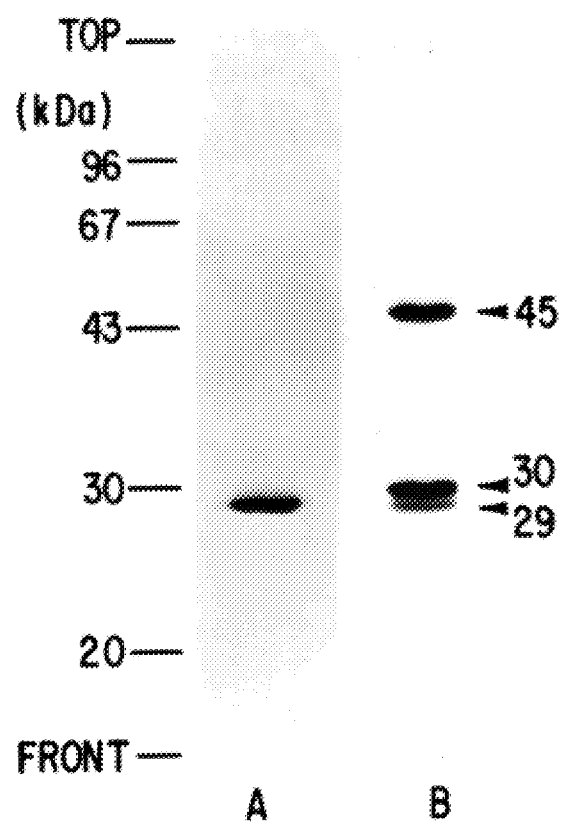
FIG. 6 is a diagram showing the results of measurement of molecular mass by SDS-PAGE.

Properties of the Oxidized Phospholipid Degrading Enzyme and Analysis of Its Structure (a) Measurement of molecular mass In step (g) of Example 1, the molecular mass of the present enzyme was determined to be about 100 kDa. When the present enzyme was subjected to an SDS-PAGE analysis at a gel concentration of 12% in the presence of 2-mercaptoethanol in accordance with the method proposed by Laemmli (Laemmli, U. K., Nature, 227, 680–685, 1970), three spots corresponding to 29 kDa, 30 kDa and 45 kDa were obtained as shown in FIG. 6.

It was suggested from the foregoing that the present enzyme has a heterotrimer structure consisting of three subunits of 29 kDa, 30 kDa and 45 kDa.

(b) Isolation of the 45 kDa subunit by heparin Sepharose

Against buffer A, 15 ml of the roughly purified fraction obtained in step (e) of Example 1 were dialyzed. The solution so dialyzed was then applied to a column (1×5 cm) of "heparin Sepharose" (product of Pharmacia AB) which had been equilibrated with buffer A, whereby about 80% of the enzyme activity passed through the column without adsorption. When the column was washed with buffer A subsequent to the passage of the dialyzed solution, the activity was gradually eluted with tailing.

After the column was washed with about 30 ml of buffer A, the enzyme was eluted with a 30 ml linear gradient of NaCl (0M to 1.5M) in buffer A. The enzyme activity was eluted around about 0.3M NaCl concentration. Those fractions were subjected to an SDS-PAGE analysis by the method of step (a), whereby three spots were observed at 20 kDa, 30 kDa and 45 kDa with respect to the flow-through fractions and two spots were observed at 29 kDa and 30 kDa with respect to the eluate fractions. Further, the fractions eluted around about 0.6M NaCl concentration gave only one spot at 45 kDa.

The eluate fraction obtained in step (b) gave a single peak at a molecular mass of about 50 kDa when analyzed in accordance with the method in step (g) of Example 1. From this, the above fraction was estimated to have a structure similar to the original enzyme except for the deletion of the 45 kDa subunit. Further, that eluate fraction had similar activity to the original enzyme.

(c) Measurement of the substrate specificity of the purified enzyme

The substrate specificity of the purified enzyme obtained in step (f) of Example 1 was investigated in relation to PAF, PC, phosphatidylethanolamine (PE), lyso PC and oxidized PC. Its degrading activity against PC, PE and lyso PC was measured in the presence 5 of 4 mM $CaCl_2$ in accordance with the method proposed by Dole et al. (Dole, V. P. and Menertz, H., J. Biol. Chem., 253, 2595 (1960)). The activity against oxidized PC and PAF was measured following the method in Reference Examples 2 and 3. The results are presented in Table 2.

TABLE 2

| Substrate Specificity | |
|---|---|
| Substrate | Specific activity (nmol/min/mg) |
| PAF | 1.45 |
| PC | Not degraded |
| PE | Not degraded |
| Lyso Pc | Not degraded |
| Oxidized PC | 0.86 |

From the results in Table 2, it has been found that the present enzyme shows degrading activity against oxidized PC and PAF, does not show any degrading activity against normal PC and PE and further shows absolutely no degrading activity against lyso PC already hydrolyzed at the 2-site. Namely, the present enzyme was estimated to act in the first step of degradation of an oxidized phospholipid.

(d) Measurement of the sensitivity of the purified enzyme to inhibitors

Portions of the purified enzyme (40 mg/ml) obtained in step (f) of Example 1 were added iodoacetamide (IAM), p-bromophenacyl bromide (BPB) and diisopropyl fluorophosphate (DFP), respectively, to give final concentrations 0.1 mM and 1 mM. After the resulting mixtures were preincubated at room temperature for 10 minutes, changes in the activity were investigated. The results are presented in Table 3.

TABLE 3

| Sensitivity to Enzyme Inhibitors | | |
|---|---|---|
| Enzyme inhibitor | Final concentration (mM) | Inhibition (%) |
| IAM | 0.1 | 0 |
|  | 1.0 | 0 |
| BPB | 0.1 | 20 |
|  | 1.0 | 97 |
| DFP | 0.1 | 96 |
|  | 1.0 | 99 |

As is shown in Table 3, the purified enzyme was strongly inhibited by DFP and was also inhibited by BPB as the concentration as high as 1 mM, but was not inhibited at all by IAM. From this, it was estimated that serine residual groups and histidine residual groups are contained as essential groups in the active center of the present enzyme.

(e) Identification of an activity-bearing subunit by [$^3$H]-labeling

Since the present purified enzyme is strongly inhibited by DFP as shown above in step (d), an activity-bearing subunit was identified using labeled DFP. Described specifically, [$^3$H]-labeled DFP (10 µCi, 1.16 nmol, product of New England Nuclear Company) was added to 50 µg of the purified enzyme (50 µl of a solution in buffer A). After the resulting mixture was incubated at room temperature for 30 minutes, an SDS-PAGE analysis was conducted following the method in step (a) of Example 2. Subsequence to CBB staining, the resulting mixture was treated for 1 hour with an enhancer ("En³Hance, product of New England Nuclear Company).

After the treatment, the gel was dried and in a form closely contacted with a film ("XRP-5", Eastman Kodak Company), was exposed to light at −70° C. for 4 days. As a result, only the 29 kDa subunit was specifically labeled. It was hence revealed that active serine residual groups were contained therein.

(f) Measurement of the pH dependency of the enzyme activity

Using the method in Reference Example 3, the enzyme activity was measured in the presence of 5 mM EDTA while varying the reaction pH 0.5 by 0.5 in a range of from 4.0 to 9.0 by changing the buffer (employed were 100 mM acetate buffer from pH 4.0 to pH 5.5, 100 mM Tris-maleate buffer from pH 5.5 to pH 7.0, and 100 mM Tris-HCl buffer from pH 7.0 to pH 9.0). As a result, the optimal pH for the present enzyme was found to range from 7.0 to 8.0

(g) Evaluation of influence of calcium ions on the enzyme activity

The enzyme activity was measured by the measuring method of Reference Example 3 except that 4 mM CaCl₂ was added instead of 5 mM of EDTA. As a result, it has been found that the enzyme activity is enhanced by about 1.3 times by the addition of calcium.

EXAMPLE 3

Determination of the Primary Structures of Peptide Fragments of the Purified Enzyme To analyze the primary structure of the present enzyme so purified, the enzyme was converted to a reduced pyridyl ethyl form and then split with API and the determination of the structures of individual peptide fragments was attempted. After the API splitting, the individual peptide fragments were recovered by reverse phase HPLC. With respect to ten peptide fragments, their structures were determined by an amino acid sequencer in accordance with a method commonly employed in the art. The amino acid sequences of the respective peptide fragments will hereinafter be indicated by SEQ. ID Nos. 10–19, respectively.

```
(SEQ. ID. No:10)
Ile  Val  Val  Val  Trp  Val  Gly  Thr  Asn  Asn  His  Gly  His  Thr  Ala  Glu
1                   5                        10                       15

(SEQ. ID. No:11)
Ala  Ile  Val  Gln  Leu  Val  Asn  Glu  Arg  Gln  Pro  Gln  Ala  Arg  Val  Val  Val
1                   5                        10                       15
Leu  Gly  Leu  Leu  Pro  Arg  Gly  Gln  His  Pro
               20                       25

(SEQ. ID. No:12)
Asp  Lys  Glu  Pro  Glu  Val  Val  Phe  Ile  Gly  Asp  Ser  Leu  Val  Gln  Leu  Met
1                   5                        10                       15
His  Gln  Cys  Glu  Ile  Trp  Arg  Gln  Leu  Phe  Ser  Pro  Leu  His  Ala  Leu  Asn
               20                       25                       30
Phe  Gly  Ile
35

(SEQ. ID. No:13)
Asp  Lys  Glu  Pro  Asp  Val  Leu  Phe  Val  Gly  Asp  Ser  Met  Val  Gln  Leu
1                   5                        10                       15

(SEQ. ID. No:14)
Ile  Ile  Val  Leu  Gly  Leu  Leu  Pro  Arg  Gly  Glu  Lys  Pro  Asn  Pro  Leu  Arg
1                   5                        10                       15
Lys
18

(SEQ. ID. No:15)
Leu  Ala  Asn  Val  Gln  Leu  Leu  Asp  Thr  Xaa  Gly  Gly  Phe  Val  His  Ser  Asp
1                   5                        10                       15
Gly  Ala  Ile  Ser  Cys  His  Asp  Met  Phe  Asp  Phe  Leu  His
               20                       25                       30

(SEQ. ID. No:16)
Val  Leu  Ser  Gln  Arg  Gln  Arg  Asp  Glu  Leu  Asn  Arg  Ala  Ile  Ala  Asp  Tyr
1                   5                        10                       15
Leu  Arg  Ser  Asn  Gly  Tyr  Glu  Glu  Ala  Tyr
               20                       25

(SEQ. ID. No:17)
Thr  Phe  Thr  Gly  His  Arg  Glu  Trp  Val  Arg  Met  Val  Arg  Pro  Asn  Gln  Asp
1                   5                        10                       15
Gly  Thr
     19

(SEQ. ID. No:18)
Thr  Leu  Asn  Ala  His  Glu  His  Phe  Val  Thr  Ser  Leu  Asp  Phe  His  Lys
1                   5                        10                       15

(SEQ. ID. No:19)
Val  Trp  Glu  Cys  Arg
1                   5
```

EXAMPLE 4

Determination of the Structures of the Respective Subunits cDNA's of the Oxidized Phospholipid degrading enzyme (a) Preparation of mRNA derived from bovine brain Using "ISOGEN" (product of WAKO PURE CHEMICAL INDUSTRIES, LTD.), RNA was prepared from bovine brain. mRNA was purified using "Oligotex-dT30<Super>" (product of Takara Shuzo Co., Ltd.

(b) Preparation of a CDNA plasmid library derived from bovine brain (1) Synthesis of first strand CDNA Using "SuperScript Plasmid System" of GIBCO Company, CDNA was synthesized from 5 μg of mRNA derived from bovine brain. First, 2 μl of an NotI dT$_{17}$ primer adapter were treated with diethyl pyrocarbonate (DEPC), added to a solution of 5 pg of mRNA in 5 μl of distilled water, heated at 70° C. for 10 minutes and then cooled on ice.

Added were 4 μl of 5× first strand buffer, 2 μl of a 0.1M DTT solution, 1 μl of 10 mM dNTPs and 1 μl of DEPC-treated distilled water, followed by incubation at 37° C. for 2 minutes. "Superscript" reverse transcriptase (5 μl) was added and subsequent to incubation for 1 hour at 37° C., the resultant mixture was placed on ice to terminate the reaction.

(2) Synthesis of second strand cDNA

To 18 μl out of the 20 μl reaction mixture employed for the synthesis of the first strand cDNA, were added 93 μl of DEPC-treated distilled water, 30 μl of 5× second strand buffer, 3 μl of 10 mM dNTPs, 1 μl of 10 U/ml $E.$ $coil$ DNA ligase, 4 μl of 10 U/ml $E.$ $coil$ DNA polymerase and 1 μl of 2U/ml $E.$ $coli$ RNaseH. The resultant mixture was incubated at 16° C. for 2 hours, to which 2 μl (10 U) of T$_4$DNA polymerase were added, followed by incubation at 16° C. for 5 minutes.

The reaction mixture was placed on ice, to which were added 10 μl of 0.5M EDTA and 150 μl of a 25:24:1 solvent of phenol, chloroform and isoamyl alcohol. Subsequent to vigorous stirring, the mixture was centrifuged at 14,000 g's for 10 minutes and 140 μl of the supernatant were transferred to a fresh centrifuge tube. The supernatant was added with 70 μl of 7.5M ammonium acetate and 0.5 ml of ethanol, stirred and then left over at −80° C. for 30 minutes. The mixture so obtained was centrifuged at 14,000 g's for 10 minutes and subsequent to removal of the supernatant, the precipitate was washed with 0.5 ml of 70% ethanol and then dried under reduced pressure.

(3) Addition of BstXI adapter

The above cDNA precipitate was dissolved in 25 μl of DEPC-treated distilled water, followed by the addition of 10 μl of 5× T$_4$DNA ligase buffer, 10 μl of BstXI adapter (product of Invitrogen Company) and 5 μl of T$_4$DNA ligase. The resulting mixture was incubated at 16° C. for 16 hours. The mixture was then added with 50 μl of a phenol-chloroform-isoamyl alcohol (25:24:1) solvent system, followed by vigorous agitation. The mixture so obtained was centrifuged at 14,000 g's for 5 minutes, and 45 μl of the supernatant were transferred to a fresh centrifuge tube.

The supernatant was added with 25 μl of 7.5M ammonium acetate and 150 μl of ethanol. The resulting mixture was stirred and then left over at −80° C. for 30 minutes. The mixture was centrifuged at 14,000 g's for 10 minutes and the supernatant was decanted. The precipitate was washed with 0.5 ml of 70% ethanol and then dried under reduced pressure.

(4) Splitting by NotI

The above cDNA precipitate was dissolved in 41 μl of DEPC-treated distilled water, to which 5 μl of REACT 7 buffer and 4 μl of NotI were added. The resultant mixture was incubated at 37° C. for 2 hours, followed by the addition of 50 μl of a phenol-chloroform-isoamyl alcohol (25:24:1) solvent system and further by vigorous stirring. The mixture so prepared was centrifuged at 14,000 g's for 10 minutes, and 45 μl of the supernatant were transferred in a fresh centrifuge tube.

(5) Removal of the adapter and size-dependent fractionation of CDNA

The above CDNA solution was fractionated using "Quick Spin Column Linker 5" (manufactured by BMY Company), so that 50 μl of 40 ng/μl cDNA were obtained.

(6) Insertion of CDNA into plasmid vector and electroporation of $E.$ $coli$

Added to 3 μl of the above CDNA solution was 1 μl of 29 ng/μl pRC/CMV vector (product of Invitrogen Company) which had been split with NotI and BstXI. Subsequent to the addition of 32 μl of Solution A and 4 μl of Solution B of the "Takara Ligation Kit", the resultant mixture was incubated at 16° C. for 30 minutes. The mixture was added with 40 μl of a phenol-chloroform-isoamyl alcohol (25:24:1) solvent system, vigorously stirred and then centrifuged at 14,000 g's for 10 minutes, and 35 μl of the supernatant were transferred to a fresh centrifuge tube.

The solution was added with 25 μl of 7.5M ammonium acetate and 150 μl of ethanol. The resulting mixture was stirred, left over at −80° C. for 30 minutes and then centrifuged at 14,000 g's for 10 minutes. After the supernant was decanted, the precipitate was washed with 0.5 ml of 70% ethanol, dried under reduced pressure and then dissolved in 5 μl of distilled water. Transformation was conducted using 50 μl of "Electro Max DH10B Competent Cell" (product by BRL Company) 206,000 clones of a recombinant were obtained. Further, using 29 mg/ml pRC/CMV vector (product of Invitrogen Company) which had been split with BstXI, 505,400 clones of a recombinant were obtained likewise.

(c) Cloning of the cDNA of the 29 kDa subunit of the oxidized phospholipid degrading enzyme by MOPAC (Mixed Oligonucleotide Primed Amplification of cDNA)

Using, as a DNA template for a PCR reaction, 5 ng of the cDNA obtained above in step (b)(5), the cDNA was added with 5 μl of 10× PCR buffer, 8 μl of 1.25 mM dNTPs and 1 μl portions of 10 OD/ml primers (SEQ. ID Nos. 20 and 21 to be described below). The total volume was brought to 49 μl with DPC-treated distilled water. After the mixture so obtained was heated at 95 ° C. for 5 minutes, 0.25 μl of 5 U/ml TaqDNA polymerase (product of Perkin ElmerCetus Company) was added. A reaction cycle consisting of 1 minute at 94° C., 2 minutes at 58° C. and 2 minutes at 72° C. was repeated 35 times, followed by incubation at 72° C. for 10 minutes.

(SEQ. ID. No:20)
    GGYTG NCKYT CRTTN AC
(SEQ. ID. No:21)
    CAYCA RTGYG ARATH TG

A band of a PCR reaction product (230 bp) was observed by 2% agarose gel electrophoresis. After mineral oil was eliminated with chloroform, excess primers and dNTP were removed using "Suprec TM02" (product of Takara Shuzo Co., Ltd.). A phenol-chloroform-isoamyl alcohol (25:24:1) solvent system was then added, followed by vigorous stirring. The resulting mixture was centrifuged at 14,000 g's for 10 minutes and 45 μl of the supernatant were transferred to a fresh centrifuge tube. The supernatant was added with 25

μl of 7.5M ammonium acetate and 150 μl of ethanol, stirred and then left over at −80° C. for 30 minutes. The mixture so obtained was centrifuged at 14,000 g's for 10 minutes. After the supernatant was decanted, the precipitate was washed with 0.5 ml of 70% ethanol, dried under reduced pressure and then dissolved in 5 μl of distilled water.

Subsequent to insertion into PCRII (product of Invitrogen Company), E. coli DH5α Max Efficiency component cells (product of BRL Company) were subjected to transformation. With respect to the plasmid DNA as the transformant, cloning was confirmed by PCR in which M13 reverse CAGGAAACAGCTATGAC (SEQ ID NO:30) and M13(−20) forward GTAAAACGACGGCCAG (SEQ ID NO:31) were used. After the cloning, culture was conducted. The plasmid DNA was purified using CsCl and ultracentrifugation. The primary structural sequence of the inserted DNA fragment was determined using M13 forward primer and M13 reverse primer (by an automated sequencer manufactured by Applied Biosystems, Inc., Model 370A).

As a result, the sequence of 231 bp corresponding to Nos. 231–461 of nucleotide of SEQ. ID. No: 4 in the Sequence Listing was clarified. It contained the 24th–37 amino acid (RELFSPLHALNFGI) of SEQ. ID. No: 12, the 1ST 12th amino acid (IVVVWVGTNNHG) of SEQ. ID. No: 10 and the 1ST 5th amino acid (AIVQL) of SEQ. ID: No. 11, all of which were identified in Example 3. It has hence been found that the PCR reaction product is a part of the cDNA of 29 kDa subunit of the oxidized phospholipid degrading enzyme.

From the two types of oligomers (below-described SEQ. ID. Nos: 22 and 23) synthesized based on the above-found base sequence of the cDNA of the 29 kDa subunit, a full-length cDNA was cloned using PCR in accordance with the method reported by Kwiatkowski, Jr., T. J., Zoghbi, H. Y., Ledbetter, S. A., Ellison, K. A. and Chinault, A. C. in Nucleic Acids Res., 18, 7191–7192, 1990.

(SEQ. ID. No:22)
    ATGTG CTGTG GCGTC TGG
(SEQ. ID. No:23)
    AGTGT GCCCG TGGTT GTT

The cDNA plasmid library derived from bovine brain, said library having been prepared in step (b)(6), was placed on a 96-well plate by diluting it to distribute 50 clones per well. Stationary culture was then conducted overnight. Culture fluid were recovered by combining together, as a single pool, the fluid portions from the wells in each of 12 columns.

Using 0.5 μl of the culture fluid as a DNA template for a PCR reaction, it was added with 5 μl of 10× PCR buffer, 8 μl of 1.25 mM dNTPs and 1 μl portions of the 10 OD/ml primers (SEQ. ID Nos. 23 and 24 described above). The total volume was brought to 49 μl with DPC-treated distilled water. After the mixture so obtained was heated at 95° C. for 5 minutes, 0.25 μl of 5 U/ml TaqDNA polymerase (product of Perkin ElmerCetus Company) was added. A reaction cycle consisting of 1 minute at 94° C., 1 minute at 58° C. and 2 minutes at 72° C. was repeated 35 times, followed by incubation at 72° C. for 10 minutes. An analysis was then conducted by 2% agarose gel electrophoresis.

With respect to each pool on which a band of a PCR reaction product (107 bp) was observed by electrophoresis, a PCR reaction was conducted further. Each pool on which a band of the PCR reaction product (107 bp) was observed was lawned on the LB agar medium and each colony was subjected to a PCR reaction to achieve cloning. After the cloning, culture was conducted, and the plasmid DNA was purified using CsCl and ultracentrifugation. The primary structural sequence of the inserted DNA fragment was then determined (by the automated sequencer manufactured by Applied Biosystems, Inc., Model 370A).

The results are presented under SEQ. ID. No: 4 in the Sequence Listing. The coding initiator methionine was considered to be the 77th nucleotide, and the 5'-untranslated region had 76 bp. The primary structural sequence of the cDNA of the 29 kDa subunit was determined. The number of amino acid residual groups in the structural gene was 232 and its estimated molecular mass was 26901.94 (including the coding initiator methionine). SEQ. ID. No: 12 was found at the amino acid numbers 36 to 72 in SEQ. ID. No: 4 in the Sequence Listing, SEQ. ID. No: 10 was found at the amino acid numbers 96 to 111 in SEQ. ID. No: 4 in the Sequence Listing, and SEQ. ID. No: 11 was found at the amino acid numbers 119 to 145 in SEQ. ID. No: 4 in the Sequence Listing.

(d) Cloning of the CDNA of the 30 kDa subunit of the oxidized phospholipid degrading enzyme by MOPAC Using as a DNA template for a PCR reaction 5 ng of the cDNA obtained in step (b)(5), the CDNA was added with 5 μl of 10× PCR buffer, 8 μl of 1.25 mM dNTPs and 1 μl portions of 10 OD/ml primers (SEQ. ID. Nos: 24 and 25 to be described below). The total volume was then brought to 49 μl with DPC-treated distilled water.

(SEQ. ID. No:24)
    AARGA RCCCN GAYGT NYT
(SEQ. ID. No:25)
    NARNG GRTTN GGYTT KT

After the above solution was heated at 95° C. for 5 minutes, 0.25 μl of 5 U/ml TaqDNA polymerase (product of Perkin ElmerCetus Company) was added. A reaction cycle consisting of 1 minute at 94° C., 1 minute at 58° C. and 2 minutes at 72° C. was conducted 35 times, followed by incubation at 72° C. for 10 minutes. An analysis was then conducted by 2% agarose gel electrophoresis.

A band of a PCR reaction product (360 bp) was observed by electrophoresis. After mineral oil was eliminated with chloroform, excess primers and dNTPs were removed using "Suprec TM02" (product of Takara Shuzo Co., Ltd.). A phenol-chloroform-isoamyl alcohol (25:24:1) solvent system was added, followed by vigorous stirring. The resulting mixture was centrifuged at 14,000 g's for 10 minutes and 45 μl of the supernatant were transferred to a fresh centrifuge tube. The supernatant was added with 25 μl of 7.5M ammonium acetate and 150 μl of ethanol, stirred and then left over at −80° C. for 30 minutes.

The mixture so obtained was centrifuged at 14,000 g's for 10 minutes. After the supernatant was decanted, the precipitate was washed with 0.5 ml of 70% ethanol, dried under reduced pressure and then dissolved in 5 μl of distilled water. Subsequent to insertion into pCRII (product of Invitrogen Company), E. coli DH5α Max Efficiency competent cells (product of BRL Company) were subjected to transformation. With respect to the plasmid DNA as the transformant, cloning was confirmed by PCR in which M13 reverse CAGGAAACAGCTATGAC (SEQ ID NO:30) and M13(−20) forward GTAAAACGACGGCCAG (SEQ ID NO:31) were used. After the cloning, culture was conducted. The plasmid DNA was purified using CsCl and ultracentrifugation. The primary structural sequence of the inserted DNA fragment was determined using M13 forward primer and M13 reverse primer (by the automated sequencer manufactured by Applied Biosystems, Inc., Model 370A).

As a result, the sequence of 336 bp corresponding to the nucleotide numbers 1 to 336 in SEQ. ID. No: 6 in the Sequence Listing has been determined. It has become clear that there are the 8th–16th-amino acids (FVGDSMVQL) of SEQ. ID. No: 13 and the 1ST–10th-amino acids (IIVLGLLPRG) of SEQ. ID. No: 14, both clarified in Example 3, and this PCR reaction product is a part of the cDNA of the 30 kDa subunit of the oxidized phospholipid degrading enzyme.

(e) Cloning of cDNA of the 45 kDa subunit of the oxidized phospholipid degrading enzyme by MOPAC.

Using as a DNA template for a PCR reaction 5 ng of the cDNA obtained in step (b)(5), the cDNA was added with 5 μl of 10× PCR buffer, 8 μl of 1.25 mM dNTPs and 1 μl portions of 10 OD/ml primers (SEQ. ID. Nos: 26 and 27 to be described below). The total volume was then brought to 49 μl with DPC-treated distilled water. After the above solution was heated at 95° C. for 5 minutes, 0.25 μl of 5 U/ml TaqDNA polymerase (product of Perkin ElmerCetus Company) was added. A reaction cycle consisting of 1 minute at 94° C., 1 minute at 58° C. and 2 minutes at 72° C. was conducted 35 times, followed by incubation at 72° C. for 10 minutes. An analysis was then conducted by 2% agarose gel electrophoresis.

(SEQ. ID. No:26)
GGNTA YGARG ARGCN TA
(SEQ. ID. No:27)
TGRTT NGGNC KNACC AT

A band of a PCR reaction product (660 bp) was observed by electrophoresis. After mineral oil was eliminated with chloroform, excess primers and dNTPs were removed using "Suprec TM02" (product of Takara Shuzo Co., Ltd.). A phenol-chloroform-isoamyl alcohol (25:24:1) solvent system was then added, followed by vigorous stirring. The resulting mixture was centrifuged at 14,000 g's for 10 minutes and 45 μl of the supernatant were transferred to a fresh centrifuge tube. The supernatant was added with 25 μl of 7.5M ammonium acetate and 150 μl of ethanol, stirred and then left over at –80° C. for 30 minutes. The mixture so obtained was centrifuged at 14,000 g's for 10 minutes. After the supernatant was decanted, the precipitate was washed with 0.5 ml of 70% ethanol, dried under reduced pressure and then dissolved in 5 μl of distilled water.

Subsequent to insertion into pCRII (product of Invitrogen Company), E. coli DH5α Max Efficiency component cells (product of BRL Company) were subjected to transformation. With respect to the plasmid DNA as the transformant, cloning was confirmed by PCR in which M13 reverse CAGGAAACAGCTATGAC (SEQ ID NO:30) and M13(-20) forward GTAAAACGACGGCCAG (SEQ ID NO:31) were used. After the cloning, culture was conducted. The plasmid DNA was purified using CsCl and ultracentrifugation. The primary structural sequence of the inserted DNA fragment was determined using M13 forward primer and M13 reverse primer (by the automated sequencer manufactured by Applied Biosystems, Inc., Model 370A).

As a result, the sequence of 664 bp corresponding to the nucleotide numbers 1020 to 1683 in SEQ. ID. No: 8 has been determined. It has become clear that there is the 1ST–10TH-amino acids (TFTGHREWVR) of SEQ. ID. No: 17, clarified in Example 3, and this PCR reaction product is a part of the cDNA of the 45 kDa subunit of the oxidized phospholipid degrading enzyme.

Two types of oligomers (below-described SEQ. ID. Nos: 28 and 29) were synthesized based on the above-found base sequence of the cDNA of the 45 kDa subunit.

(SEQ. ID. No:28)
AAGAG ACCCA AAAGA ATG
(SEQ. ID. No:29)
GCACT TCCCA CATTT TTA

Using these oligomers, a full-length cDNA was cloned using PCR in accordance with the method reported by Kwiatkowski, Jr., T. J., Zoghbi, H. Y., Ledbetter, S. A., Ellison, K. A. and Chinault, A. C. in Nucleic Acids Res., 18, 7191–7192, 1990.

The cDNA plasmid library derived from bovine brain, said library having been prepared in step (b)(6), was placed on a 96-well plate by diluting it to distribute 50 clones per well. Stationary culture was then conducted overnight. Culture fluid were recovered by combining together, as a single pool, the fluid portions from the wells in each of 12 columns. Using 0.5 μl of the culture fluid as a DNA template for a PCR reaction, it was added with 5 μl of 10× PCR buffer, 8 μl of 1.25 mM dNTPs and 1 μl portions of the 10 OD/ml primers (SEQ. ID Nos. 29 and 30 described above). The total volume was brought to 49 μl with DPC-treated distilled water. After the mixture so obtained was heated at 95 ° C. for 5 minutes, 0.25 μl of 5 U/ml TaqDNA polymerase (product of Perkin ElmerCetus Company) was added. A reaction cycle consisting of 1 minute at 94° C., 1 minute at 58° C. and 2 minutes at 72° C. was repeated 35 times, followed by incubation at 72° C. for 10 minutes. An analysis was then conducted by 2% agarose gel electrophoresis.

With respect to each pool on which a band of a PCR reaction product (400 bp) was observed by electrophoresis, a PCR reaction was conducted further. Each pool on which a band of the PCR reaction product (400 bp) was observed was lawned and each colony was subjected to a PCR reaction to achieve cloning. After the cloning, culture was conducted, and the plasmid DNA was purified using CsCl and ultracentrifugation. The primary structural sequence of the inserted DNA fragment was then determined (by the automated sequencer manufactured by Applied Biosystems, Inc., Model 370A).

The results are presented under SEQ. ID. No: 8 in the Sequence Listing. The coding initiator methionine was considered to be the 843rd nucleotide, and the 5'-untranslated region had 842 bp. The primary structural sequence of the cDNA of the 45 kDa subunit was determined. The number of amino acid residual groups in the structural gene was 410 and its estimated molecular mass was 46667.68 (including the coding initiator methionine). SEQ. ID. No: 16 was found at the amino acid numbers 2 to 28 in SEQ. ID. No: 8 in the Sequence Listing, SEQ. ID. No: 17 was found at the amino acid numbers 229 to 247 in SEQ. ID. No: 8 in the Sequence Listing, SEQ. ID. No: 18 was found at the amino acid numbers 375 to 390 in SEQ. ID. No: 8 in the Sequence Listing, and SEQ. ID. No: 19 was found at the amino acid numbers 406 to 410 in SEQ. ID. No: 8 in the Sequence Listing.

We claim:

1. An isolated polynucleotide encoding the polypeptide of SEQ ID No: 1.

2. The polynucleotide of claim 1 wherein the polynucleotide comprises residues 80 to 772 of SEQ ID No:4.

3. An isolated polynucleotide encoding the polypeptide of SEQ ID No:2.

4. The polynucleotide of claim 3 wherein the polynucleotide comprises residues 1 to 336 of SEQ ID No:6.

5. An isolated polynucleotide encoding the polypeptide of SEQ ID No:3.

6. The polynucleotide of claim 5 wherein the polynucleotide comprises residues 847 to 2073 of SEQ ID No:8.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
( A ) LENGTH: 231 amino acids
( B ) TYPE: amino acid
( C ) STRANDEDNESS: unknown
( D ) TOPOLOGY: unknown ( i i ) MOLECULE TYPE: peptide ( v i ) ORIGINAL SOURCE:
( A ) ORGANISM: Bos taurus ( x i ) SEQUENCE DESCRIPTION: SEQ ID NO:1:

| Ser 1 | Gly | Asp | Glu | Asn 5 | Pro | Ala | Ser | Lys | Pro 10 | Thr | Pro | Val | Gln | Asp 15 | Val |
|---|---|---|---|---|---|---|---|---|---|---|---|---|---|---|---|
| Gln | Gly | Asp | Gly 20 | Arg | Trp | Met | Ser | Leu 25 | His | His | Arg | Phe | Val 30 | Ala | Asp |
| Ser | Lys | Asp 35 | Lys | Glu | Pro | Glu | Val 40 | Val | Phe | Ile | Gly | Asp 45 | Ser | Leu | Val |
| Gln | Leu 50 | Met | His | Gln | Cys | Glu 55 | Ile | Trp | Arg | Glu | Leu 60 | Phe | Ser | Pro | Leu |
| His 65 | Ala | Leu | Asn | Phe | Gly 70 | Ile | Gly | Gly | Asp | Ser 75 | Thr | Gln | His | Val | Leu 80 |
| Trp | Arg | Leu | Glu | Asn 85 | Gly | Glu | Leu | Glu | His 90 | Ile | Arg | Pro | Lys | Ile 95 | Val |
| Val | Val | Trp | Val 100 | Gly | Thr | Asn | Asn | His 105 | Gly | His | Thr | Ala | Glu 110 | Gln | Val |
| Thr | Gly | Gly 115 | Ile | Lys | Ala | Ile | Val 120 | Gln | Leu | Val | Asn | Glu 125 | Arg | Gln | Pro |
| Gln | Ala 130 | Arg | Val | Val | Val | Leu 135 | Gly | Leu | Leu | Pro | Arg 140 | Gly | Gln | His | Pro |
| Thr 145 | Gln | Leu | Arg | Glu | Lys 150 | Asn | Arg | Arg | Val | Asn 155 | Glu | Leu | Val | Arg | Ala 160 |
| Ala | Leu | Ala | Gly | His 165 | Pro | Arg | Ala | His | Phe 170 | Leu | Asp | Ala | Asp | Pro 175 | Gly |
| Phe | Val | His | Ser 180 | Asp | Gly | Thr | Ile | Ser 185 | His | His | Asp | Met | Tyr 190 | Asp | Tyr |
| Leu | His | Leu 195 | Ser | Arg | Leu | Gly | Tyr 200 | Thr | Pro | Val | Cys | Arg 205 | Ala | Leu | His |
| Ser | Leu 210 | Leu | Leu | Arg | Leu | Leu 215 | Thr | Gln | Asp | Gln | Gly 220 | Gln | Gly | Gly | Ala |
| Pro 225 | Leu | Pro | Glu | Pro | Ser 230 | Pro | | | | | | | | | |

( 2 ) INFORMATION FOR SEQ ID NO:2:

( i ) SEQUENCE CHARACTERISTICS:
( A ) LENGTH: 112 amino acids
( B ) TYPE: amino acid
( C ) STRANDEDNESS: unknown
( D ) TOPOLOGY: unknown ( i i ) MOLECULE TYPE: peptide ( v i ) ORIGINAL SOURCE:

(A) ORGANISM: Bos taurus (xi) SEQUENCE DESCRIPTION: SEQ ID NO:2:

| Lys | Glu | Pro | Asp | Val | Leu | Phe | Val | Gly | Asp | Ser | Met | Val | Gln | Leu | Met |
|---|---|---|---|---|---|---|---|---|---|---|---|---|---|---|---|
| 1 | | | | 5 | | | | | 10 | | | | | 15 | |
| Gln | Gln | Tyr | Glu | Ile | Trp | Arg | Glu | Leu | Phe | Ser | Pro | Leu | His | Ala | Leu |
| | | | 20 | | | | 25 | | | | | 30 | | | |
| Asn | Phe | Gly | Ile | Gly | Gly | Asp | Thr | Thr | Arg | His | Val | Leu | Trp | Arg | Leu |
| | | 35 | | | | | 40 | | | | | 45 | | | |
| Lys | Asn | Gly | Glu | Leu | Glu | Asn | Ile | Lys | Pro | Lys | Val | Ile | Val | Val | Trp |
| | 50 | | | | | 55 | | | | | 60 | | | | |
| Val | Gly | Thr | Asn | Asn | His | Glu | Asn | Thr | Ala | Glu | Glu | Val | Ala | Gly | Gly |
| 65 | | | | | 70 | | | | 75 | | | | | | 80 |
| Ile | Glu | Ala | Ile | Val | Gln | Leu | Ile | Asn | Thr | Arg | Gln | Pro | Gln | Ala | Lys |
| | | | | 85 | | | | | 90 | | | | | 95 | |
| Ile | Ile | Val | Leu | Gly | Leu | Leu | Pro | Arg | Gly | Glu | Lys | Pro | Asn | Pro | Leu |
| | | | 100 | | | | | 105 | | | | | 110 | | |

(2) INFORMATION FOR SEQ ID NO:3:

(i) SEQUENCE CHARACTERISTICS:
(A) LENGTH: 409 amino acids
(B) TYPE: amino acid
(C) STRANDEDNESS: unknown
(D) TOPOLOGY: unknown (ii) MOLECULE TYPE: peptide (vi) ORIGINAL SOURCE:
(A) ORGANISM: Bos taurus (xi) SEQUENCE DESCRIPTION: SEQ ID NO:3:

| Val | Leu | Ser | Gln | Arg | Gln | Arg | Asp | Glu | Leu | Asn | Arg | Ala | Ile | Ala | Asp |
|---|---|---|---|---|---|---|---|---|---|---|---|---|---|---|---|
| 1 | | | | 5 | | | | | 10 | | | | | 15 | |
| Tyr | Leu | Arg | Ser | Asn | Gly | Tyr | Glu | Glu | Ala | Tyr | Ser | Val | Phe | Lys | Lys |
| | | | 20 | | | | | 25 | | | | | 30 | | |
| Glu | Ala | Glu | Leu | Asp | Met | Asn | Glu | Glu | Leu | Asp | Lys | Lys | Tyr | Ala | Gly |
| | | | 35 | | | | 40 | | | | | 45 | | | |
| Leu | Leu | Glu | Lys | Lys | Trp | Thr | Ser | Val | Ile | Arg | Leu | Gln | Lys | Lys | Val |
| | 50 | | | | | 55 | | | | | 60 | | | | |
| Met | Glu | Leu | Glu | Ser | Lys | Leu | Asn | Glu | Ala | Lys | Glu | Glu | Phe | Thr | Ser |
| 65 | | | | | 70 | | | | 75 | | | | | | 80 |
| Gly | Gly | Pro | Leu | Gly | Gln | Lys | Arg | Asp | Pro | Lys | Glu | Trp | Ile | Pro | Arg |
| | | | | 85 | | | | | 90 | | | | | 95 | |
| Pro | Pro | Glu | Lys | Tyr | Ala | Leu | Ser | Gly | His | Arg | Ser | Pro | Val | Thr | Arg |
| | | | 100 | | | | | 105 | | | | | 110 | | |
| Val | Ile | Phe | His | Pro | Val | Phe | Ser | Val | Met | Val | Ser | Ala | Ser | Glu | Asp |
| | | | 115 | | | | | 120 | | | | | 125 | | |
| Ala | Thr | Ile | Lys | Val | Trp | Asp | Tyr | Glu | Thr | Gly | Asp | Phe | Glu | Arg | Thr |
| | | | 130 | | | | | 135 | | | | | 140 | | |
| Leu | Lys | Gly | His | Thr | Asp | Ser | Val | Gln | Asp | Ile | Ser | Phe | Asp | His | Ser |
| 145 | | | | | 150 | | | | | 155 | | | | | 160 |
| Gly | Lys | Leu | Leu | Ala | Ser | Cys | Ser | Ala | Asp | Met | Thr | Ile | Lys | Leu | Trp |
| | | | | 165 | | | | | 170 | | | | | 175 | |
| Asp | Phe | Gln | Gly | Phe | Glu | Cys | Ile | Arg | Thr | Met | His | Gly | His | Asp | His |
| | | | 180 | | | | | 185 | | | | | 190 | | |
| Asn | Val | Ser | Ser | Val | Ala | Ile | Met | Pro | Asn | Gly | Asp | His | Ile | Val | Ser |
| | | | 195 | | | | | 200 | | | | | 205 | | |

| | | | | | | | | | | | | | | |
|---|---|---|---|---|---|---|---|---|---|---|---|---|---|---|
| Ala | Ser | Arg | Asp | Lys | Thr | Ile | Lys | Met | Trp | Glu | Val | Gln | Thr | Gly | Tyr |
| | 210 | | | | | 215 | | | | | 220 | | | | |
| Cys | Val | Lys | Thr | Phe | Thr | Gly | His | Arg | Glu | Trp | Val | Arg | Met | Val | Arg |
| 225 | | | | | 230 | | | | | 235 | | | | | 240 |
| Pro | Asn | Gln | Asp | Gly | Thr | Leu | Ile | Ala | Ser | Cys | Ser | Asn | Asp | Gln | Thr |
| | | | | 245 | | | | | 250 | | | | | 255 | |
| Val | Arg | Val | Trp | Val | Val | Ala | Thr | Lys | Glu | Cys | Lys | Ala | Glu | Leu | Arg |
| | | | 260 | | | | | 265 | | | | | 270 | | |
| Glu | His | Glu | His | Val | Val | Glu | Cys | Ile | Ser | Trp | Ala | Pro | Glu | Ser | Ser |
| | | 275 | | | | | 280 | | | | | 285 | | | |
| Tyr | Ser | Ser | Ile | Ser | Glu | Ala | Thr | Gly | Ser | Glu | Thr | Lys | Lys | Ser | Gly |
| | 290 | | | | | 295 | | | | | 300 | | | | |
| Lys | Pro | Gly | Pro | Phe | Leu | Leu | Ser | Gly | Ser | Arg | Asp | Lys | Thr | Ile | Lys |
| 305 | | | | | 310 | | | | | 315 | | | | | 320 |
| Met | Trp | Asp | Val | Ser | Thr | Gly | Met | Cys | Leu | Met | Thr | Leu | Val | Gly | His |
| | | | | 325 | | | | | 330 | | | | | 335 | |
| Asp | Asn | Trp | Val | Arg | Gly | Val | Leu | Phe | His | Ser | Gly | Gly | Lys | Phe | Ile |
| | | | 340 | | | | | 345 | | | | | 350 | | |
| Leu | Ser | Cys | Ala | Asp | Asp | Lys | Thr | Leu | Arg | Val | Trp | Asp | Tyr | Lys | Asn |
| | | 355 | | | | | 360 | | | | | 365 | | | |
| Lys | Arg | Cys | Met | Lys | Thr | Leu | Asn | Ala | His | Glu | His | Phe | Val | Thr | Ser |
| | 370 | | | | | 375 | | | | | 380 | | | | |
| Leu | Asp | Phe | His | Lys | Thr | Ala | Pro | Tyr | Val | Val | Thr | Gly | Ser | Val | Asp |
| 385 | | | | | 390 | | | | | 395 | | | | | 400 |
| Gln | Thr | Val | Lys | Val | Trp | Glu | Cys | Arg | | | | | | | |
| | | | | 405 | | | | | | | | | | | |

( 2 ) INFORMATION FOR SEQ ID NO:4:

( i ) SEQUENCE CHARACTERISTICS:
        ( A ) LENGTH: 820 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: Bos taurus ( i x ) FEATURE:
        ( A ) NAME/KEY: CDS
        ( B ) LOCATION: 77..772

( x i ) SEQUENCE DESCRIPTION: SEQ ID NO:4:

```
TGGTTTCTTC  CCCCAGGACT  GGCGCTAGAT  TTCCCCCGCC  TACTCTCGGC  CTTCAGGAGC              60

GGAGGCGAGT  GGCAAG ATG AGT GGA GAC GAG AAC CCA GCC AGC AAG CCC                     109
                   Met Ser Gly Asp Glu Asn Pro Ala Ser Lys Pro
                    1               5                      10

ACG CCA GTG CAG GAC GTG CAG GGT GAC GGG CGC TGG ATG TCC CTG CAC                    157
Thr Pro Val Gln Asp Val Gln Gly Asp Gly Arg Trp Met Ser Leu His
             15                  20                  25

CAT CGG TTC GTA GCC GAC AGC AAA GAT AAG GAA CCC GAA GTC GTC TTC                    205
His Arg Phe Val Ala Asp Ser Lys Asp Lys Glu Pro Glu Val Val Phe
         30                  35                  40

ATC GGT GAC TCC TTG GTC CAG CTG ATG CAC CAG TGC GAG ATC TGG CGG                    253
Ile Gly Asp Ser Leu Val Gln Leu Met His Gln Cys Glu Ile Trp Arg
     45                  50                  55

GAG CTC TTT TCC CCT CTG CAC GCA CTT AAC TTT GGC ATT GGC GGT GAC                    301
Glu Leu Phe Ser Pro Leu His Ala Leu Asn Phe Gly Ile Gly Gly Asp
 60                  65                  70                  75
```

```
AGC ACA CAG CAT GTG CTG TGG CGT CTG GAG AAT GGA GAG CTG GAA CAC     349
Ser Thr Gln His Val Leu Trp Arg Leu Glu Asn Gly Glu Leu Glu His
            80                      85                      90

ATC CGG CCC AAG ATT GTG GTG GTC TGG GTT GGT ACC AAC AAC CAC GGG     397
Ile Arg Pro Lys Ile Val Val Val Trp Val Gly Thr Asn Asn His Gly
        95                      100                     105

CAC ACT GCA GAG CAG GTG ACT GGG GGC ATC AAG GCC ATA GTG CAG CTG     445
His Thr Ala Glu Gln Val Thr Gly Gly Ile Lys Ala Ile Val Gln Leu
            110                     115                     120

GTG AAC GAG CGG CAG CCC CAG GCA CGG GTC GTG GTG CTG GGC CTG CTT     493
Val Asn Glu Arg Gln Pro Gln Ala Arg Val Val Val Leu Gly Leu Leu
        125                     130                     135

CCT CGG GGC CAG CAC CCC ACC CAA CTT CGA GAG AAA AAC CGA CGG GTG     541
Pro Arg Gly Gln His Pro Thr Gln Leu Arg Glu Lys Asn Arg Arg Val
140                     145                     150                     155

AAT GAG CTG GTA CGG GCA GCA CTG GCC GGC CAC CCT CGG GCC CAC TTC     589
Asn Glu Leu Val Arg Ala Ala Leu Ala Gly His Pro Arg Ala His Phe
            160                     165                     170

CTG GAC GCA GAC CCT GGC TTT GTG CAC TCA GAT GGT ACC ATC AGC CAC     637
Leu Asp Ala Asp Pro Gly Phe Val His Ser Asp Gly Thr Ile Ser His
            175                     180                     185

CAT GAC ATG TAC GAT TAC CTG CAC CTG AGC CGT CTG GGG TAC ACA CCT     685
His Asp Met Tyr Asp Tyr Leu His Leu Ser Arg Leu Gly Tyr Thr Pro
            190                     195                     200

GTT TGC CGG GCC CTG CAC TCC TTG CTT CTG CGT CTG CTA ACC CAA GAC     733
Val Cys Arg Ala Leu His Ser Leu Leu Leu Arg Leu Leu Thr Gln Asp
        205                     210                     215

CAG GGA CAG GGT GGT GCC CCC CTG CCG GAA CCC AGC CCC TAAGCATCTG      782
Gln Gly Gln Gly Gly Ala Pro Leu Pro Glu Pro Ser Pro
220                     225                     230

TCTTCCTACA ACATTAAATT TTCATTTTTC AGTCAAAA                            820

( 2 ) INFORMATION FOR SEQ ID NO:5:

( i ) SEQUENCE CHARACTERISTICS:
                ( A ) LENGTH: 232 amino acids
                ( B ) TYPE: amino acid
                ( D ) TOPOLOGY: linear ( i i ) MOLECULE TYPE: protein ( x i ) SEQUENCE DESCRIPTION: SEQ ID NO:5:

Met Ser Gly Asp Glu Asn Pro Ala Ser Lys Pro Thr Pro Val Gln Asp
 1               5                  10                      15

Val Gln Gly Asp Gly Arg Trp Met Ser Leu His His Arg Phe Val Ala
            20                      25                      30

Asp Ser Lys Asp Lys Glu Pro Glu Val Val Phe Ile Gly Asp Ser Leu
        35                      40                      45

Val Gln Leu Met His Gln Cys Glu Ile Trp Arg Glu Leu Phe Ser Pro
    50                      55                      60

Leu His Ala Leu Asn Phe Gly Ile Gly Gly Asp Ser Thr Gln His Val
65                      70                      75                      80

Leu Trp Arg Leu Glu Asn Gly Glu Leu Glu His Ile Arg Pro Lys Ile
            85                      90                      95

Val Val Val Trp Val Gly Thr Asn Asn His Gly His Thr Ala Glu Gln
            100                     105                     110

Val Thr Gly Gly Ile Lys Ala Ile Val Gln Leu Val Asn Glu Arg Gln
        115                     120                     125

Pro Gln Ala Arg Val Val Val Leu Gly Leu Leu Pro Arg Gly Gln His
```

|     |     |     |     |     | 130 |     |     |     |     | 135 |     |     |     |     | 140 |     |
|-----|-----|-----|-----|-----|-----|-----|-----|-----|-----|-----|-----|-----|-----|-----|-----|-----|

Pro Thr Gln Leu Arg Glu Lys Asn Arg Arg Val Asn Glu Leu Val Arg
145                     150                 155                 160

Ala Ala Leu Ala Gly His Pro Arg Ala His Phe Leu Asp Ala Asp Pro
                165             170                 175

Gly Phe Val His Ser Asp Gly Thr Ile Ser His His Asp Met Tyr Asp
            180             185                 190

Tyr Leu His Leu Ser Arg Leu Gly Tyr Thr Pro Val Cys Arg Ala Leu
        195                 200             205

His Ser Leu Leu Leu Arg Leu Leu Thr Gln Asp Gln Gly Gln Gly Gly
    210                 215             220

Ala Pro Leu Pro Glu Pro Ser Pro
225                 230

( 2 ) INFORMATION FOR SEQ ID NO:6:

( i ) SEQUENCE CHARACTERISTICS:
        ( A ) LENGTH: 336 base pairs
        ( B ) TYPE: nucleic acid
        ( C ) STRANDEDNESS: unknown
        ( D ) TOPOLOGY: unknown ( i i ) MOLECULE TYPE: cDNA ( v i ) ORIGINAL SOURCE:
        ( A ) ORGANISM: Bos taurus ( i x ) FEATURE:
        ( A ) NAME/KEY: CDS
        ( B ) LOCATION: 1..336

( x i ) SEQUENCE DESCRIPTION: SEQ ID NO:6:

AAG GAG CCG GAT GTC CTG TTC GTG GGG GAC TCC ATG GTA CAG TTG ATG    48
Lys Glu Pro Asp Val Leu Phe Val Gly Asp Ser Met Val Gln Leu Met
1               5                   10                  15

CAG CAG TAT GAG ATA TGG CGA GAG CTT TTT TCT CCA CTT CAT GCA CTG    96
Gln Gln Tyr Glu Ile Trp Arg Glu Leu Phe Ser Pro Leu His Ala Leu
            20                  25                  30

AAT TTT GGA ATT GGG GGA GAT ACA ACA AGA CAT GTT TTA TGG AGA CTT   144
Asn Phe Gly Ile Gly Gly Asp Thr Thr Arg His Val Leu Trp Arg Leu
        35                  40                  45

AAG AAT GGA GAA CTG GAG AAT ATT AAA CCT AAG GTC ATC GTT GTC TGG   192
Lys Asn Gly Glu Leu Glu Asn Ile Lys Pro Lys Val Ile Val Val Trp
    50                  55                  60

GTA GGA ACA AAC AAC CAT GAA AAT ACA GCA GAG GAA GTA GCA GGT GGA   240
Val Gly Thr Asn Asn His Glu Asn Thr Ala Glu Glu Val Ala Gly Gly
65                  70                  75                  80

ATC GAG GCC ATC GTA CAG CTT ATC AAC ACA AGG CAG CCA CAG GCC AAA   288
Ile Glu Ala Ile Val Gln Leu Ile Asn Thr Arg Gln Pro Gln Ala Lys
                85                  90                  95

ATC ATT GTA TTG GGT TTG TTA CCT CGA GGT GAG AAG CCC AAC CCT CTC   336
Ile Ile Val Leu Gly Leu Leu Pro Arg Gly Glu Lys Pro Asn Pro Leu
            100                 105                 110

( 2 ) INFORMATION FOR SEQ ID NO:7:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Lys Glu Pro Asp Val Leu Phe Val Gly Asp Ser Met Val Gln Leu Met
 1               5                   10                  15

Gln Gln Tyr Glu Ile Trp Arg Glu Leu Phe Ser Pro Leu His Ala Leu
            20                  25                  30

Asn Phe Gly Ile Gly Gly Asp Thr Thr Arg His Val Leu Trp Arg Leu
        35                  40                  45

Lys Asn Gly Glu Leu Glu Asn Ile Lys Pro Lys Val Ile Val Val Trp
        50                  55                  60

Val Gly Thr Asn Asn His Glu Asn Thr Ala Glu Glu Val Ala Gly Gly
 65                 70                  75                  80

Ile Glu Ala Ile Val Gln Leu Ile Asn Thr Arg Gln Pro Gln Ala Lys
                85                  90                  95

Ile Ile Val Leu Gly Leu Leu Pro Arg Gly Glu Lys Pro Asn Pro Leu
                100                 105                 110
```

(2) INFORMATION FOR SEQ ID NO:8:

(i) SEQUENCE CHARACTERISTICS:
        (A) LENGTH: 2085 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Bos taurus (ix) FEATURE:
        (A) NAME/KEY: CDS
        (B) LOCATION: 844..2073

(xi) SEQUENCE DESCRIPTION: SEQ ID NO:8:

```
GCGGCCGCGA CGGCCGTTGA GTGAGAGACA CGGGAGGAGG GGGGGACAGG CCGGGTAGGG      60

CGCTGCCCTC GCTCCCCTCC TCCCTGGCCC GGGTTCTGGG GGTGCCAGGG CCGCCGCGGC     120

TCCACCCGCG GCCTTCCCCG GGAAGGGATC GCCTTCCTCC CTTGGTGACT TAGCAAGAAA     180

AGTATTCTTG GGTAGGAAGG GCGTGGGGAG CAGGTCCCTC TCAGATCTTG GGGAGAGGGT     240

TCGGCTCTCC TCTCCCTGTC CGCGGGAGAG AAGCTCCGCA GTCCCCACCC CGCCCCGCGG     300

CTGGCGCTCA GGGACCGGGC TCAAGCCTCC TCGGCACTGT CCACCGGCCT GCAGGCGTTC     360

TGTCCCCCAC CTGTCCTTAG GATGGAGTTG ACCTGAGAAG GATGGTCCAG CCTTTCCCTG     420

GCCCCCCTAT GCGGTGGTTC AGCCCCTGCA CCCACTGAGG AGGAGCGGCC TGACCCCACC     480

GAACCATCCG CAGCATCCAC CCACCAAATC CGGCAGGATT TTCTTTTCTG CCGTCGGCTC     540

CTTCAACGGG AGCTGCCTTT TGACGTTGTA ACACTGAGCT TCGAGGCCCT CAGCCATTCT     600

CCTTCGAATC TCCCCACTCG TATAGGAAAC GCAGTGCCTG CCTTAACCTC CCAGGTGGAA     660

TGAACCTTAC TTGTTGAATA TCTCCTGGTT ACACGTTGGA TTCACTTGTG AAAGAATCAT     720

TTTCCCCTGC GTGAAAGCCA CTTAGTGGCT TATTAATTAT AAATCCAGGG GTTGCAAAGC     780

TTTTTGATTT TCCAGAGGAG GGACATAACC ACTATATCGA ATAAGCTTGA TATTACAGCC     840

AAA ATG GTG CTG TCC CAG AGA CAA CGA GAT GAA CTA AAT CGA GCT ATA      888
    Met Val Leu Ser Gln Arg Gln Arg Asp Glu Leu Asn Arg Ala Ile
     1               5                   10                  15

GCA GAT TAT CTT CGT TCA AAT GGC TAC GAA GAA GCA TAT TCA GTT TTT      936
Ala Asp Tyr Leu Arg Ser Asn Gly Tyr Glu Glu Ala Tyr Ser Val Phe
                20                  25                  30

AAA AAG GAA GCT GAA TTA GAT ATG AAT GAA GAA TTA GAT AAG AAA TAT      984
Lys Lys Glu Ala Glu Leu Asp Met Asn Glu Glu Leu Asp Lys Lys Tyr
                35                  40                  45
```

| | | | | | | | | | | | | | | | | |
|---|---|---|---|---|---|---|---|---|---|---|---|---|---|---|---|---|
| GCT | GGT | CTT | TTG | GAA | AAA | AAA | TGG | ACA | TCT | GTT | ATT | AGA | TTA | CAA | AAG | 1032 |
| Ala | Gly | Leu | Leu | Glu | Lys | Lys | Trp | Thr | Ser | Val | Ile | Arg | Leu | Gln | Lys | |
| | | 50 | | | | 55 | | | | | 60 | | | | | |
| AAG | GTT | ATG | GAA | TTA | GAA | TCA | AAG | TTA | AAT | GAA | GCA | AAA | GAA | GAA | TTT | 1080 |
| Lys | Val | Met | Glu | Leu | Glu | Ser | Lys | Leu | Asn | Glu | Ala | Lys | Glu | Glu | Phe | |
| | 65 | | | | | 70 | | | | | 75 | | | | | |
| ACG | TCG | GGT | GGA | CCT | CTT | GGT | CAG | AAA | AGA | GAC | CCA | AAA | GAA | TGG | ATT | 1128 |
| Thr | Ser | Gly | Gly | Pro | Leu | Gly | Gln | Lys | Arg | Asp | Pro | Lys | Glu | Trp | Ile | |
| 80 | | | | | 85 | | | | | 90 | | | | | 95 | |
| CCC | CGT | CCA | CCA | GAA | AAA | TAT | GCA | TTG | AGT | GGT | CAT | AGG | AGT | CCA | GTC | 1176 |
| Pro | Arg | Pro | Pro | Glu | Lys | Tyr | Ala | Leu | Ser | Gly | His | Arg | Ser | Pro | Val | |
| | | | | 100 | | | | | 105 | | | | | 110 | | |
| ACT | CGA | GTC | ATT | TTC | CAT | CCT | GTG | TTC | AGT | GTT | ATG | GTC | TCT | GCT | TCA | 1224 |
| Thr | Arg | Val | Ile | Phe | His | Pro | Val | Phe | Ser | Val | Met | Val | Ser | Ala | Ser | |
| | | | 115 | | | | | 120 | | | | | 125 | | | |
| GAG | GAT | GCT | ACA | ATT | AAG | GTG | TGG | GAT | TAT | GAG | ACT | GGA | GAT | TTT | GAA | 1272 |
| Glu | Asp | Ala | Thr | Ile | Lys | Val | Trp | Asp | Tyr | Glu | Thr | Gly | Asp | Phe | Glu | |
| | | | 130 | | | | | 135 | | | | | 140 | | | |
| CGA | ACT | CTT | AAG | GGG | CAT | ACA | GAC | TCT | GTA | CAG | GAT | ATT | TCA | TTC | GAC | 1320 |
| Arg | Thr | Leu | Lys | Gly | His | Thr | Asp | Ser | Val | Gln | Asp | Ile | Ser | Phe | Asp | |
| 145 | | | | | 150 | | | | | | 155 | | | | | |
| CAC | AGT | GGC | AAG | CTT | CTG | GCT | TCA | TGT | TCT | GCA | GAT | ATG | ACC | ATT | AAG | 1368 |
| His | Ser | Gly | Lys | Leu | Leu | Ala | Ser | Cys | Ser | Ala | Asp | Met | Thr | Ile | Lys | |
| 160 | | | | | 165 | | | | | 170 | | | | | 175 | |
| CTA | TGG | GAT | TTT | CAG | GGC | TTT | GAA | TGC | ATC | AGA | ACC | ATG | CAT | GGC | CAT | 1416 |
| Leu | Trp | Asp | Phe | Gln | Gly | Phe | Glu | Cys | Ile | Arg | Thr | Met | His | Gly | His | |
| | | | | 180 | | | | | 185 | | | | | 190 | | |
| GAC | CAC | AAT | GTT | TCT | TCA | GTA | GCC | ATC | ATG | CCC | AAT | GGA | GAT | CAT | ATA | 1464 |
| Asp | His | Asn | Val | Ser | Ser | Val | Ala | Ile | Met | Pro | Asn | Gly | Asp | His | Ile | |
| | | | 195 | | | | | 200 | | | | | 205 | | | |
| GTG | TCT | GCC | TCA | AGG | GAT | AAA | ACT | ATA | AAA | ATG | TGG | GAA | GTG | CAA | ACT | 1512 |
| Val | Ser | Ala | Ser | Arg | Asp | Lys | Thr | Ile | Lys | Met | Trp | Glu | Val | Gln | Thr | |
| | | | 210 | | | | | 215 | | | | | 220 | | | |
| GGC | TAC | TGT | GTG | AAG | ACA | TTC | ACA | GGA | CAC | AGA | GAA | TGG | GTA | CGT | ATG | 1560 |
| Gly | Tyr | Cys | Val | Lys | Thr | Phe | Thr | Gly | His | Arg | Glu | Trp | Val | Arg | Met | |
| | | 225 | | | | | 230 | | | | | 235 | | | | |
| GTG | CGG | CCA | AAT | CAA | GAC | GGC | ACT | CTG | ATA | GCC | AGC | TGT | TCC | AAT | GAC | 1608 |
| Val | Arg | Pro | Asn | Gln | Asp | Gly | Thr | Leu | Ile | Ala | Ser | Cys | Ser | Asn | Asp | |
| 240 | | | | | 245 | | | | | 250 | | | | | 255 | |
| CAG | ACT | GTG | CGT | GTA | TGG | GTC | GTA | GCA | ACA | AAG | GAA | TGC | AAG | GCT | GAG | 1656 |
| Gln | Thr | Val | Arg | Val | Trp | Val | Val | Ala | Thr | Lys | Glu | Cys | Lys | Ala | Glu | |
| | | | | 260 | | | | | 265 | | | | | 270 | | |
| CTT | CGA | GAA | CAT | GAG | CAT | GTG | GTA | GAA | TGC | ATT | TCC | TGG | GCT | CCT | GAA | 1704 |
| Leu | Arg | Glu | His | Glu | His | Val | Val | Glu | Cys | Ile | Ser | Trp | Ala | Pro | Glu | |
| | | | 275 | | | | | 280 | | | | | 285 | | | |
| AGC | TCA | TAT | TCT | TCC | ATC | TCT | GAA | GCA | ACA | GGA | TCT | GAG | ACT | AAA | AAA | 1752 |
| Ser | Ser | Tyr | Ser | Ser | Ile | Ser | Glu | Ala | Thr | Gly | Ser | Glu | Thr | Lys | Lys | |
| | | 290 | | | | | 295 | | | | | 300 | | | | |
| AGT | GGC | AAA | CCT | GGG | CCA | TTC | TTA | CTG | TCC | GGA | TCC | AGG | GAC | AAG | ACT | 1800 |
| Ser | Gly | Lys | Pro | Gly | Pro | Phe | Leu | Leu | Ser | Gly | Ser | Arg | Asp | Lys | Thr | |
| | 305 | | | | | 310 | | | | | 315 | | | | | |
| ATC | AAG | ATG | TGG | GAT | GTC | AGT | ACT | GGC | ATG | TGC | CTT | ATG | ACC | CTG | GTG | 1848 |
| Ile | Lys | Met | Trp | Asp | Val | Ser | Thr | Gly | Met | Cys | Leu | Met | Thr | Leu | Val | |
| 320 | | | | | 325 | | | | | 330 | | | | | 335 | |
| GGT | CAT | GAT | AAC | TGG | GTA | CGT | GGA | GTT | CTG | TTC | CAT | TCT | GGG | GGG | AAG | 1896 |
| Gly | His | Asp | Asn | Trp | Val | Arg | Gly | Val | Leu | Phe | His | Ser | Gly | Gly | Lys | |
| | | | | 340 | | | | | 345 | | | | | 350 | | |
| TTT | ATT | TTG | AGT | TGC | GCT | GAT | GAC | AAG | ACC | CTG | CGC | GTG | TGG | GAT | TAC | 1944 |
| Phe | Ile | Leu | Ser | Cys | Ala | Asp | Asp | Lys | Thr | Leu | Arg | Val | Trp | Asp | Tyr | |
| | | | 355 | | | | | 360 | | | | | 365 | | | |

|     |     |     |     |     |     |     |     |     |     |     |     |     |     |     |     |
|-----|-----|-----|-----|-----|-----|-----|-----|-----|-----|-----|-----|-----|-----|-----|-----|
| AAG | AAC | AAG | CGA | TGC | ATG | AAG | ACC | CTC | AAT | GCG | CAT | GAA | CAC | TTT | GTT | 1992
| Lys | Asn | Lys | Arg | Cys | Met | Lys | Thr | Leu | Asn | Ala | His | Glu | His | Phe | Val |
|     |     | 370 |     |     |     | 375 |     |     |     |     | 380 |     |     |     |     |
| ACC | TCC | TTG | GAT | TTC | CAT | AAG | ACG | GCC | CCA | TAT | GTG | GTT | ACT | GGC | AGT | 2040
| Thr | Ser | Leu | Asp | Phe | His | Lys | Thr | Ala | Pro | Tyr | Val | Val | Thr | Gly | Ser |
|     | 385 |     |     |     |     | 390 |     |     |     |     | 395 |     |     |     |     |
| GTA | GAT | CAA | ACA | GTA | AAG | GTG | TGG | GAG | TGT | CGT | TGATTGAGTC | TC | | | | 2085
| Val | Asp | Gln | Thr | Val | Lys | Val | Trp | Glu | Cys | Arg |  |  |  |  |  |
| 400 |     |     |     | 405 |     |     |     |     |     | 410 |  |  |  |  |  |

( 2 ) INFORMATION FOR SEQ ID NO:9:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Val | Leu | Ser | Gln | Arg | Gln | Arg | Asp | Glu | Leu | Asn | Arg | Ala | Ile | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asp | Tyr | Leu | Arg | Ser | Asn | Gly | Tyr | Glu | Glu | Ala | Tyr | Ser | Val | Phe | Lys |
|     |     |     | 20  |     |     |     |     | 25  |     |     |     |     | 30  |     |     |
| Lys | Glu | Ala | Glu | Leu | Asp | Met | Asn | Glu | Glu | Leu | Asp | Lys | Lys | Tyr | Ala |
|     |     |     | 35  |     |     |     | 40  |     |     |     |     | 45  |     |     |     |
| Gly | Leu | Leu | Glu | Lys | Lys | Trp | Thr | Ser | Val | Ile | Arg | Leu | Gln | Lys | Lys |
|     | 50  |     |     |     |     | 55  |     |     |     |     | 60  |     |     |     |     |
| Val | Met | Glu | Leu | Glu | Ser | Lys | Leu | Asn | Glu | Ala | Lys | Glu | Glu | Phe | Thr |
| 65  |     |     |     |     | 70  |     |     |     |     | 75  |     |     |     |     | 80  |
| Ser | Gly | Gly | Pro | Leu | Gly | Gln | Lys | Arg | Asp | Pro | Lys | Glu | Trp | Ile | Pro |
|     |     |     |     | 85  |     |     |     |     | 90  |     |     |     |     | 95  |     |
| Arg | Pro | Pro | Glu | Lys | Tyr | Ala | Leu | Ser | Gly | His | Arg | Ser | Pro | Val | Thr |
|     |     |     |     | 100 |     |     |     |     | 105 |     |     |     |     | 110 |     |
| Arg | Val | Ile | Phe | His | Pro | Val | Phe | Ser | Val | Met | Val | Ser | Ala | Ser | Glu |
|     |     |     | 115 |     |     |     |     | 120 |     |     |     |     | 125 |     |     |
| Asp | Ala | Thr | Ile | Lys | Val | Trp | Asp | Tyr | Glu | Thr | Gly | Asp | Phe | Glu | Arg |
|     |     | 130 |     |     |     |     | 135 |     |     |     |     | 140 |     |     |     |
| Thr | Leu | Lys | Gly | His | Thr | Asp | Ser | Val | Gln | Asp | Ile | Ser | Phe | Asp | His |
| 145 |     |     |     |     | 150 |     |     |     |     | 155 |     |     |     |     | 160 |
| Ser | Gly | Lys | Leu | Leu | Ala | Ser | Cys | Ser | Ala | Asp | Met | Thr | Ile | Lys | Leu |
|     |     |     |     | 165 |     |     |     |     | 170 |     |     |     |     | 175 |     |
| Trp | Asp | Phe | Gln | Gly | Phe | Glu | Cys | Ile | Arg | Thr | Met | His | Gly | His | Asp |
|     |     |     | 180 |     |     |     |     | 185 |     |     |     |     | 190 |     |     |
| His | Asn | Val | Ser | Ser | Val | Ala | Ile | Met | Pro | Asn | Gly | Asp | His | Ile | Val |
|     |     | 195 |     |     |     |     | 200 |     |     |     |     | 205 |     |     |     |
| Ser | Ala | Ser | Arg | Asp | Lys | Thr | Ile | Lys | Met | Trp | Glu | Val | Gln | Thr | Gly |
|     | 210 |     |     |     |     | 215 |     |     |     |     | 220 |     |     |     |     |
| Tyr | Cys | Val | Lys | Thr | Phe | Thr | Gly | His | Arg | Glu | Trp | Val | Arg | Met | Val |
| 225 |     |     |     |     | 230 |     |     |     |     | 235 |     |     |     |     | 240 |
| Arg | Pro | Asn | Gln | Asp | Gly | Thr | Leu | Ile | Ala | Ser | Cys | Ser | Asn | Asp | Gln |
|     |     |     |     | 245 |     |     |     |     | 250 |     |     |     |     | 255 |     |
| Thr | Val | Arg | Val | Trp | Val | Val | Ala | Thr | Lys | Glu | Cys | Lys | Ala | Glu | Leu |
|     |     |     | 260 |     |     |     |     | 265 |     |     |     |     | 270 |     |     |
| Arg | Glu | His | Glu | His | Val | Val | Glu | Cys | Ile | Ser | Trp | Ala | Pro | Glu | Ser |
|     |     | 275 |     |     |     |     | 280 |     |     |     |     | 285 |     |     |     |
| Ser | Tyr | Ser | Ser | Ile | Ser | Glu | Ala | Thr | Gly | Ser | Glu | Thr | Lys | Lys | Ser |

-continued

```
                  290                           295                           300
Gly  Lys  Pro  Gly  Pro  Phe  Leu  Leu  Ser  Gly  Ser  Arg  Asp  Lys  Thr  Ile
305                           310                          315                          320

Lys  Met  Trp  Asp  Val  Ser  Thr  Gly  Met  Cys  Leu  Met  Thr  Leu  Val  Gly
                         325                          330                          335

His  Asp  Asn  Trp  Val  Arg  Gly  Val  Leu  Phe  His  Ser  Gly  Gly  Lys  Phe
                         340                          345                          350

Ile  Leu  Ser  Cys  Ala  Asp  Asp  Lys  Thr  Leu  Arg  Val  Trp  Asp  Tyr  Lys
               355                           360                          365

Asn  Lys  Arg  Cys  Met  Lys  Thr  Leu  Asn  Ala  His  Glu  His  Phe  Val  Thr
          370                           375                          380

Ser  Leu  Asp  Phe  His  Lys  Thr  Ala  Pro  Tyr  Val  Val  Thr  Gly  Ser  Val
385                           390                          395                          400

Asp  Gln  Thr  Val  Lys  Val  Trp  Glu  Cys  Arg
                    405                          410
```

( 2 ) INFORMATION FOR SEQ ID NO:10:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:10:

```
Ile  Val  Val  Val  Trp  Val  Gly  Thr  Asn  His  Gly  His  Thr  Ala  Glu
1                    5                          10                         15
```

( 2 ) INFORMATION FOR SEQ ID NO:11:

( i ) SEQUENCE CHARACTERISTICS:
        ( A ) LENGTH: 27 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

```
Ala  Ile  Val  Gln  Leu  Val  Asn  Glu  Arg  Gln  Pro  Gln  Ala  Arg  Val  Val
1                    5                          10                         15

Val  Leu  Gly  Leu  Leu  Pro  Arg  Gly  Gln  His  Pro
               20                          25
```

( 2 ) INFORMATION FOR SEQ ID NO:12:

( i ) SEQUENCE CHARACTERISTICS:
        ( A ) LENGTH: 37 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
Asp  Lys  Glu  Pro  Glu  Val  Val  Phe  Ile  Gly  Asp  Ser  Leu  Val  Gln  Leu
1                    5                          10                         15

Met  His  Gln  Cys  Glu  Ile  Trp  Arg  Glu  Leu  Phe  Ser  Pro  Leu  His  Ala
                    20                          25                         30

Leu  Asn  Phe  Gly  Ile
               35
```

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

```
Asp Lys Glu Pro Asp Val Leu Phe Val Gly Asp Ser Met Val Gln Leu
1               5                   10                  15
```

( 2 ) INFORMATION FOR SEQ ID NO:14:

( i ) SEQUENCE CHARACTERISTICS:
        ( A ) LENGTH: 18 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:14:

```
Ile Ile Val Leu Gly Leu Leu Pro Arg Gly Glu Lys Pro Asn Pro Leu
1               5                   10                  15

Arg Lys
```

( 2 ) INFORMATION FOR SEQ ID NO:15:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:15:

```
Leu Ala Asn Val Gln Leu Leu Asp Thr Xaa Gly Gly Phe Val His Ser
1               5                   10                  15

Asp Gly Ala Ile Ser Cys His Asp Met Phe Asp Phe Leu His
                20                  25                  30
```

( 2 ) INFORMATION FOR SEQ ID NO:16:

( i ) SEQUENCE CHARACTERISTICS:
        ( A ) LENGTH: 27 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:16:

```
Val Leu Ser Gln Arg Gln Arg Asp Glu Leu Asn Arg Ala Ile Ala Asp
1               5                   10                  15

Tyr Leu Arg Ser Asn Gly Tyr Glu Glu Ala Tyr
                20                  25
```

( 2 ) INFORMATION FOR SEQ ID NO:17:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:17:

Thr Phe Thr Gly His Arg Glu Trp Val Arg Met Val Arg Pro Asn Gln
1               5                   10                  15
Asp Gly Thr ( 2 ) INFORMATION FOR SEQ ID NO:18:

( i ) SEQUENCE CHARACTERISTICS:
( A ) LENGTH: 16 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:18:

Thr Leu Asn Ala His Glu His Phe Val Thr Ser Leu Asp Phe His Lys
1               5                   10                  15

( 2 ) INFORMATION FOR SEQ ID NO:19:

( i ) SEQUENCE CHARACTERISTICS:
( A ) LENGTH: 5 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:19:

Val Trp Glu Cys Arg
1               5

( 2 ) INFORMATION FOR SEQ ID NO:20:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: Other nucleic acid ( x i ) SEQUENCE DESCRIPTION: SEQ ID NO:20:

GGYTGNCKYT CRTTNAC                                                          17

( 2 ) INFORMATION FOR SEQ ID NO:21:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: Other nucleic acid ( x i ) SEQUENCE DESCRIPTION: SEQ ID NO:21:

CAYCARTGYG ARATHTG                                                          17

( 2 ) INFORMATION FOR SEQ ID NO:22:

( i ) SEQUENCE CHARACTERISTICS:
( A ) LENGTH: 18 base pairs
( B ) TYPE: nucleic acid
( C ) STRANDEDNESS: unknown
( D ) TOPOLOGY: unknown (ii) MOLECULE TYPE: Other nucleic acid (xi) SEQUENCE DESCRIPTION: SEQ ID NO:22:

ATGTGCTGTG GCGTCTGG                                                           18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:23:

AGTGTGCCCG TGGTTGTT                                                           18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:24:

AARGARCCCN GAYGTNYT                                                           18

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:25:

NARNGGRTTN GGYTTKT                                                            17

(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:26:

GGNTAYGARG ARGCNTA                                                            17

(2) INFORMATION FOR SEQ ID NO:27:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:27:

TGRTTNGGNC KNACCAT 17

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:28:

AAGAGACCCA AAAGAATG 18

(2) INFORMATION FOR SEQ ID NO:29:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:29:

GCACTTCCCA CATTTTTA 18

(2) INFORMATION FOR SEQ ID NO:30:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:30:

CAGGAAACAG CTATGAC 17

(2) INFORMATION FOR SEQ ID NO:31:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: Other nucleic acid (xi) SEQUENCE DESCRIPTION: SEQ ID NO:31:

GTAAAACGAC GGCCAG 16